(12) United States Patent
Everaerts et al.

(10) Patent No.: US 6,652,970 B1
(45) Date of Patent: Nov. 25, 2003

(54) DEGRADABLE CROSSLINKERS, COMPOSITIONS THEREFROM, AND METHODS OF THEIR PREPARATION AND USE

(75) Inventors: Albert I. Everaerts, Oakdale, MN (US); Charles M. Leir, Falcon Heights, MN (US); Roger A. Mader, Stillwater, MN (US); Peter A. Stark, Cottage Grove, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/612,016

(22) Filed: Jul. 7, 2000

(51) Int. Cl.[7] .............................................. B32B 9/04
(52) U.S. Cl. .................... 428/411.1; 428/501; 428/502; 428/521; 428/522; 428/524; 156/82; 156/283; 156/309.6; 156/309.9; 156/325; 156/326; 156/331.3; 522/33; 522/36; 522/39
(58) Field of Search ............................ 428/411.1, 501, 428/502, 521, 522, 524; 156/331.3, 82, 283, 309.6, 309.9, 325, 326; 522/33, 36, 39

(56) References Cited

U.S. PATENT DOCUMENTS

| | | | |
|---|---|---|---|
| RE24,906 E | 12/1960 | Ulrich | 526/328.5 |
| 3,097,944 A | 7/1963 | Riddell et al. | 504/283 |
| 3,098,002 A | 7/1963 | Riddell | 504/156 |
| 3,098,003 A | 7/1963 | Riddell | 504/156 |
| 3,239,478 A | 3/1966 | Harlan, Jr. | 428/349 |
| 3,435,003 A | 3/1969 | Craven et al. | 525/445 |
| 3,558,309 A | 1/1971 | Laridon et al. | 430/281.1 |
| 3,639,517 A | 2/1972 | Kitchen et al. | 525/314 |
| 3,772,262 A | 11/1973 | Clementi | 528/500 |
| 3,909,497 A | 9/1975 | Hendry et al. | 528/503 |
| 3,932,328 A | 1/1976 | Korpman | 524/271 |
| 4,181,752 A | 1/1980 | Martens et al. | 427/516 |
| 4,221,884 A | 9/1980 | Bi et al. | 525/314 |
| 4,303,485 A | 12/1981 | Levens | 522/12 |
| 4,329,384 A | 5/1982 | Vesley et al. | 428/41.3 |
| 4,330,590 A | 5/1982 | Vesley | 428/336 |
| 4,379,201 A | 4/1983 | Heilmann et al. | 428/345 |
| 4,444,953 A | 4/1984 | St. Clair | 525/98 |
| 4,554,324 A | 11/1985 | Husman et al. | 525/301 |
| 4,556,464 A | 12/1985 | St. Clair | 524/274 |
| 4,617,354 A | 10/1986 | Augustin et al. | 525/301 |
| 4,737,559 A | 4/1988 | Kellen et al. | 526/291 |
| 5,260,411 A | 11/1993 | Tesoro et al. | 528/353 |
| 5,322,731 A | 6/1994 | Callahan, Jr. et al. | 428/327 |
| 5,407,971 A | 4/1995 | Everaerts et al. | 522/35 |
| 5,641,856 A | 6/1997 | Meurs | 528/310 |
| 5,804,610 A | 9/1998 | Hamer et al. | 522/182 |
| 6,475,316 B1 * | 11/2002 | Kirk et al. | 156/82 |

FOREIGN PATENT DOCUMENTS

| | | |
|---|---|---|
| EP | 0 372 602 B1 | 4/1996 |
| EP | 0 853 092 A1 | 7/1998 |
| GB | 1180846 * | 2/1970 |
| JP | 52-129795 | 10/1977 |
| JP | 63-260912 | 10/1988 |
| SU | 1046242 A * | 10/1983 |
| WO | WO 95/00576 | 1/1995 |
| WO | WO 97/07161 | 2/1997 |
| WO | WO 99/03642 | 1/1999 |
| WO | WO 99/42536 | 8/1999 |
| WO | WO 00/06533 | 2/2000 |

OTHER PUBLICATIONS

Li et al "Photodecoupling . . . " Macromolecules 1990, 23, 2704–2709.*

Li et al. "Imaging . . . " 571 Journal of Imaging Science 34 (1990) Nov./Dec. No. 6.*

M.Y. Li, et al, "Imaging by Photodecoupling of Crosslinks in Polymer Gels", J. Imaging Sci., vol. 34, No. 6, 1990, pp. 259–264, XP000172579.

Min Yu Li, et al. "Photodecoupling of Cross–Links in Polymeric Gels", Macromolecules, vol. 23, No. 10, 1990, pp. 2774–2709, XP002169841.

Database WPI, Section Ch, Week 198808, Derwent Publications Ltd., London, GB; Class A21, AN 1988–054848, XP002169842 & SU 1 321 730 A (UKR Correspondence Poly), Jul. 7, 1987, Abstract, XP 002169842.

P.L. Paytash, et al., "Itaconic Acid Derivatives of 4–Aminophenyl (Alkyl or Aryl) Sulfone", Journal of the American Chemical Society, vol. 76, 1954, pp. 3500–3501, XP002170172.

P.L. Paytash, et al. "Itaconoic Acid Derivatives of Sulfanilamide", Journal of the American Chemical Society, vol. 74, 1952, pp. 4549–4552, XP002170173.

*Journal of Polymer Science Part A: Polymer Chemistry*, "Thermally Reversible Crosslinking of Polystyrene via the Furan–Maleimide Diels–Alder Reaction," vol. 30, pp. 1755–1759 (1992).

*Macromolecules*, "Reversible Gelation of Polyoxazoline by Means of Diels–Alder Reaction," vol. 23, pp. 2636–2641 (1990).

*Journal of Thermal Spray Technology*, K. A. Gross, et al, "Liquid Flame Spraying for Glass Coloring," 8, 583–589 (1999).

*Kirk–Othmer Encyclopedia of Chemical Technology*, "coating Processes (Powder Technology)," 4th Edition, Wiley: 1993, vol. 6, pp. 635–636.

*Kirk–Othmer Encyclopedia of Chemical Technology*, "Elastomers, Synthetic–Styrene–Butadiene Rubber," 4th Edition, Wiley: 1994, vol. 9, pp. 15–37.

* cited by examiner

Primary Examiner—Leszek Kiliman
(74) Attorney, Agent, or Firm—Nancy M. Lambert

(57) ABSTRACT

The present invention is directed toward compositions that are chemically different after application to a substrate as compared to the composition prior to its application. A method of the invention comprises a method of transitioning a crosslinked polymer composition from a first chemical state to a second chemical state. Advantageously, compositions of the invention are relatively stable after transformation to their altered, or second, chemical state.

27 Claims, No Drawings

DEGRADABLE CROSSLINKERS, COMPOSITIONS THEREFROM, AND METHODS OF THEIR PREPARATION AND USE

FIELD OF THE INVENTION

The present invention relates generally to crosslinkers useful in preparing crosslinked polymer compositions and further compositions therefrom.

BACKGROUND OF THE INVENTION

Polymers are generally crosslinked to increase the cohesive strength, rigidity, heat resistance, or solvent resistance of a polymer composition. However, the use of certain crosslinkers can make it difficult to apply the compositions to a substrate in, for example, the form of a coating. Certain compositions that are hot-MELT processable materials must have a sufficiently low viscosity upon melting, such that they can be readily hot-melt processed (e.g., applied to a substrate). The presence of crosslinks in a material generally increases the melt viscosity of the material, many times making it impossible to hot-melt process the materials.

In an attempt to provide materials having sufficient cohesive strength and/or rigidity, as well as processability, thermally reversible crosslinks have been used. It is well known to incorporate thermally reversible crosslinks into polymers. Upon heating, the crosslinks dissociate or break. Upon cooling, the crosslinks reform. This sequence can be performed repeatedly. Thermally reversible crosslinks find many uses, for example, in hot-melt processable and re-moldable (or recyclable) materials. By incorporating thermally reversible crosslinks into polymers, a composition can be heated to form a coating or mold from the composition and then return to its original crosslinked state.

For examples of thermally reversibly crosslinked polymers, see U.S. Pat. No. 3,435,003 (Craven); U.S. Pat. No. 4,617,354 (Augustin et al.); and U.S. Pat. No. 5,641,856 (Meurs). Also see, PCT Publication Numbers WO 95/00,576 (Heyboer) and WO 99/42,536 (Stark et al.), as well as Canary et al., "Thermally Reversible Crosslinking of Polystyrene via the Furan-Maleimide Diels-Alder Reaction," *Journal of Polymer Science Part A: Polymer Chemistry*, Vol. 30, pp. 1755–9 (1992) and Chujo et al., "Reversible Gelation of Polyoxazoline by Means of Diels-Alder Reaction," *Macromolecules*, Vol. 23, pp. 2636–41 (1990).

Further examples of thermally reversibly crosslinked polymers are thermoplastic elastomers, such as those described in *Kirk-Othmer Encyclopedia of Chemical Technology*, 4$^{th}$ Edition, Wiley: 1994, Vol. 9, pages 15–37. Such thermoplastic elastomers have many of the physical properties of rubbers (e.g., softness, flexibility, and resilience), but, in contrast to conventional rubbers, they are hot-melt processable. With such thermoplastic elastomers, the transition from a processable hot-melt to a solid, rubberlike composition is rapid, reversible, and takes place upon cooling.

Such thermoplastic elastomers are often multiphase compositions in which the phases are intimately dispersed. In many cases, the phases are chemically bonded by block- or graft-polymerization. At least one phase consists of a material is that is relatively hard or glassy at room temperature, but becomes rubbery upon heating. Another phase consists of a softer material that is rubberlike at room temperature (i.e., an elastomer). For example, a simple structure of a multiphase thermoplastic elastomer is an A-B-A block copolymer, where A is a hard phase and B is an elastomer (e.g., poly(styrene-b-elastomer-b-styrene)). Examples of these materials are included in, for example, U.S. Pat. No. 3,639,517 (Kitchen et al.) and U.S. Pat. No. 4,221,884 (Bi et al.), and Japanese Patent Publication Number 52[11977]-129795. References describing the use of these materials in formulating adhesives include, for example, U.S. Pat. No. 4,444,953 (St. Clair); U.S. Pat. No. 4,556,464 (St. Clair); U.S. Pat. No. 3,239,478 (Harlan); and U.S. Pat. No. 3,932,328 (Korpman).

It may be desired, however, to provide a composition that is chemically and/or physically different (e.g., having different adhesive properties) after application to a substrate as compared to the composition prior to its application. For example, U.S. Pat. No. 5,322,731 (Callahan, Jr. et al.) describes adhesive beads comprising a pressure-sensitive adhesive (PSA) core and a discontinuous organic polymer shell that makes the bead essentially non-tacky at room temperature. Upon application of heat and/or pressure to the bead, the core and shell materials can be blended to form a resultant PSA. By providing compositions that are essentially non-tacky before application, easier handling of the compositions is facilitated. That is, conventional handling and coating equipment, such as hopper feeders, powder conveyers, and hot-melt stick applicators can be used, without requiring specialized handling and coating equipment.

However, when using the adhesive beads described by Callahan, Jr. et al., the core and shell materials must be selected both such that they are respectively tacky and non-tacky to the touch at room temperature and such that, upon application, they combine to result in a composition having PSA properties. Furthermore, when the tacky core materials are uncrosslinked, the beads tend to be deformable, especially under pressure or at high temperatures. The shell could potentially rupture due to this deformation, causing the beads to prematurely agglomerate. As another example, see U.S. Pat. No. 5,804,610 (Hamer et As an alternative to the multi-layer constructions of, for example, Callahan, Jr. et al. and Hamer et al., U.S. Pat. No. 3,909,497 (Hendry et al.) describes solid polymers that are thermally degradable to flowable (or at least softened) compositions. The polymers contain heat-sensitive groups that cleave at a temperature substantially lower than that at which the thermal degradation would occur in their absence. Cleavage is effected essentially in the absence of materials reactive with the resulting molecular fragments. The degradation products are useful as adhesives, plasticizers, fillers, etc.

Heat-sensitive groups of Hendry et al. are taught to be azo groups, carbonate groups, ester groups, and amine-oxide groups conforming to specific formulas recited therein. However, azo groups and amine-oxide groups typically fragment into fragments containing free radicals or fragments (containing ethylenic unsaturation) susceptible to free radical polymerization, which are disadvantageously susceptible to recombination and degradation (e.g., affecting weatherability and durability of the resulting composition). The same applies to ester groups and carbonate groups, depending on their particular chemistry. Those of ordinary skill in the art will recognize that fragmentation of ester groups and carbonate groups of hydroxy compounds having active β-hydrogens, as taught by Hendry et al., results in fragments containing ethylenic unsaturation.

PCT Application Number US99/06,007 (Everaerts et al.) describes a base copolymer that exhibits little or no tack prior to its combination with a plasticizing agent. Thus, the base copolymer can be transported and processed without special handling and processing equipment. However, formulation latitude is also compromised with those compositions because the base copolymer is typically a high glass transition temperature, Tg (i.e., a Tg of at least about 0° C.), high shear storage modulus (i.e., a shear storage modulus of at least about $5 \times 10^5$ Pascals when measured at 23° C. and 1 Hertz) base copolymer in order for useful pressure-sensitive adhesive materials to be formed when the base copolymer is combined with the plasticizing agent.

Further compositions that are chemically different (e.g., leading to compositions having different adhesive properties) after application to a substrate as compared to the composition prior to its application are desired. It is also desired to provide formulations that are relatively stable after transformation to their altered chemical state, as compared to, for example, the compositions of Hendry et al. that contain free radicals or fragments containing ethylenic unsaturation that are susceptible to recombination or degradation.

SUMMARY OF THE INVENTION

The present invention is directed toward compositions that are chemically different after application to a substrate as compared to the composition prior to its application. Advantageously, compositions of the invention are relatively stable after transformation to their altered chemical state.

Degradable crosslinkers of the invention are useful in such compositions. In one embodiment of the invention, a degradable crosslinker comprises at least one energetically labile moiety and at least two free radically polymerizable groups, wherein the degradable crosslinker is capable of fragmentation into at least two fragments upon activation by an external energy source, and wherein the at least two fragments are essentially free of free radicals and ethylenic unsaturation. For example, compositions containing such degradable crosslinkers may be indicative of those in a first chemical state, prior to applying the compositions to a substrate.

A wide variety of degradable crosslinkers of this nature are provided. For example, the crosslinker can comprise at least two energetically labile moieties. The energetically labile moieties may be the same or different. In one embodiment, the energetically labile moiety comprises an ester moiety. For example, the energetically labile moiety may be an amide ester or aldoxime ester moiety.

In preferred embodiments, the crosslinker is storage-stable until activation thereof. Activation of the degradable crosslinker occurs using any suitable energy source. In one embodiment, the crosslinker is a thermally degradable crosslinker, wherein the degradable crosslinker degrades upon activation by a thermal energy source.

The chemical nature of the crosslinker is preferably selected according to the chemical nature of the polymer that it is intended to be incorporated into or that it is incorporated into (in the case of compositions comprising the degradable crosslinker). In preferred embodiments, the crosslinker is a (meth)acrylate degradable crosslinker.

Crosslinked polymer compositions comprising at least one polymer and at least one such degradable crosslinker incorporated into the at least one polymer are also disclosed. In further embodiments, the compositions can comprise at least two degradable crosslinkers incorporated into the polymer. The crosslinked polymer compositions may also comprise at least one non-degradable crosslinker.

The crosslinked polymer compositions can be tacky to the touch or essentially nontacky at room temperature. In certain embodiments, the composition is at least partially tacky at room temperature. Tackiness of the composition is adjustable by tailoring the composition according to the desired application. Certain applications benefit from providing the composition in a free-flowing form. To facilitate this form, the composition may further comprise at least one of a dusting agent and a coating agent.

A method of the invention comprises a method of transitioning a crosslinked polymer composition from a first chemical state to a second chemical state, the method comprising the steps of: (1) providing at least one crosslinked polymer composition described above and (2) activating at least a portion of the crosslinked polymer composition by applying an external energy source to at least a portion of the crosslinked polymer composition to fragment at least a portion of the degradable crosslinker.

In preferred embodiments of this method, the external energy source is a thermal energy source. The step of activating can occur prior to applying the crosslinked polymer composition to at least a portion of a substrate, while applying the crosslinked polymer composition to at least a portion of a substrate, or after applying the crosslinked polymer composition to at least a portion of a substrate.

According to this method, further steps may also be performed. For example, the method can further comprise the step of catalyzing fragmentation of the at least one degradable crosslinker. The method can further comprise the step of applying the crosslinked polymer composition to at least a portion of a substrate. After application to the substrate, the crosslinked polymer composition can be at least partially recrosslinked.

Also disclosed are polymer compositions comprising a polymer and at least two pendant moieties on the polymer, wherein the pendant moieties are the reaction product of fragmentation of the degradable crosslinker and wherein the pendant moieties comprise the at least two fragments that are essentially free of free radicals and ethylenic unsaturation. For example, compositions of this nature may be indicative of those in the second chemical state.

DETAILED DESCRIPTION OF THE PREFERRED EMBODIMENTS

Crosslinkers of the invention are useful for providing a wide variety of compositions that are chemically different (e.g., having different adhesive properties) after activation and, optionally, application to a substrate, as compared to the composition prior to its activation. As a result of a change from a first chemical state to a second chemical state, certain physical properties of the composition are altered.

In one embodiment, the crosslinkers are useful for providing compositions having varying levels of tack and/or compliance, and therefore adhesion, before and after activation of the composition (i.e., fragmentation of at least a portion of the crosslinkers in the composition). The varying levels of tack and compliance may enable tapes, for example, incorporating the compositions to be more easily repositionable and/or removable before activation as compared to after activation. Furthermore, varying levels of tack may facilitate easier handling and processing of the composition.

According to one aspect of this embodiment, a crosslinked polymer composition is essentially non-tacky before activation, but becomes tacky, enabling it to be used as an adhesive (e.g., a pressure-sensitive adhesive), after activation. According to another aspect of this embodiment, the crosslinked polymer composition is tacky before activation, becoming even more tacky after activation. Thus, multi-layer constructions, such as those described by Callahan, Jr. et al. (U.S. Pat. No. 5,322,731) and Hamer et al. (U.S. Pat. No. 5,804,610), are advantageously not necessary with the present invention.

In a preferred embodiment, the crosslinked polymer composition is "free-flowing" before activation. "Free-flowing" crosslinked polymer compositions are those compositions containing a multitude of solid state particulates that do not substantially agglomerate (i.e., the particulates are capable of being moved by gravitational forces alone) at temperatures below the activation temperature of the degradable crosslinkers. Free-flowing crosslinked polymer compositions contribute to easier feeding and delivery methods. For example, free-flowing crosslinked polymer compositions facilitate feeding hot-melt coating compositions. Furthermore, shipping and handling associated with free-flowing crosslinked polymer compositions is typically less expensive and more convenient than shipping and handling associated with bulk polymer compositions.

In another embodiment, crosslinked polymer compositions (e.g., adhesives, varnishes, waxes, paints, various coatings, such as protective and decorative coatings, etc.) of the invention can be used to provide compositions having varying levels of solvent resistance or solubility. After activation, crosslinked polymer compositions of the invention tend to be more soluble and less solvent resistant, enhancing their ability to be degraded for easier removability from articles on which they are incorporated. For example, the compositions can be made more soluble (e.g., etchable) after activation, facilitating their use in forming patterned coatings. Furthermore, when used as, for example, repulpable adhesives, the crosslinkers provide compositions having varying levels of solvent resistance or solubility, such that, after activation, the compositions tend to be more soluble and less solvent resistant, enhancing their ability to be degraded for recycling of the articles in which they are incorporated.

In another embodiment, crosslinked polymer compositions of the invention can be used to alter the failure mode of certain compositions. Typically, for example, after activation, adhesive compositions containing crosslinkers of the invention tend to fail more cohesively, as opposed to failing adhesively.

A wide variety of other uses for crosslinkers and crosslinked polymer compositions of the invention will be apparent to those of ordinary skill in the art. Generally, the crosslinkers and compositions of the invention are useful in any application where a change from a first chemical state to a second chemical state is desired.

Crosslinkers

Compositions of the invention contains degradable crosslinkers, but may include other types of crosslinkers as well. "Degradable crosslinkers" are those crosslinkers comprising at least one covalent bond, wherein the covalent bond fragments (or degrades) irreversibly (i.e., the fragments cannot recombine in any manner and they cannot react with any other portion of the polymer in which they are incorporated to form a new covalent crosslink) upon activation. Depending on the exact chemical nature of the degradable crosslinker, fragmentation may occur, for example, by an elimination or cyclization chemical reaction.

At least two fragments remain incorporated as pendant moieties on the polymer in which the degradable crosslinker was incorporated. In some embodiments, however, more than two fragments are produced and not all of the fragments remain incorporated as pendant moieties on the polymer. Nevertheless, the sum of the molecular weights of the total fragments is essentially the same as the molecular weight of the degradable crosslinker prior to fragmentation.

The degradable crosslinkers are generally storage-stable until activation. "Storage-stable" degradable crosslinkers and compositions containing degradable crosslinkers are those degradable crosslinkers that remain essentially unfragmented (or crosslinked in the case of compositions containing the degradable crosslinkers) when formed and until activation of the degradable crosslinker (also referred to as "activation of the composition").

The shelf life of the degradable crosslinker is generally long enough to permit the use of the degradable crosslinker and compositions therefrom in the desired application. Preferably, the shelf life of the degradable crosslinker is at least about three days, more preferably at least about one month, even more preferably at least about six months, and most preferably at least about one year. That is, the degradable crosslinkers do not prematurely fragment to substantially affect properties of the composition in which they reside.

Activation of the degradable crosslinker occurs by application of an external energy source (e.g., heat or thermal radiation, as well as ultraviolet radiation) to the degradable crosslinker. Typically, and preferably, the external energy source is a thermal energy source (e.g., heat). Thus, preferred degradable crosslinkers are thermally degradable crosslinkers.

"Thermally degradable crosslinkers" typically fragment according to the invention when subjected to temperatures greater than the polymerization temperature of the polymer in which they are integrated, preferably when subjected to temperatures at least about 20° C. greater than the polymerization temperature of the polymer in which they are incorporated. Preferably, the degradable crosslinker fragments at a temperature less than the temperature at which the polymer in which it is integrated degrades (i.e., the temperature at which the polymer becomes useless for its intended purpose, such as by uncontrollably crosslinking or charring).

The temperature at which a thermally degradable crosslinker fragments within about two hours or less is referred to as its "activation temperature." When incorporated into polymers, the activation temperature of the crosslinked polymer composition is typically the same as the activation temperature of the thermally degradable crosslinker (or the thermally degradable crosslinker having the lowest activation temperature) incorporated therein. Preferably, the activation temperature is about 80° C. to about 200° C., more preferably about 80° C. to about 180° C. Compositions containing the degradable crosslinkers are subjected to any suitable temperature to transform the composition from a first chemical state into the desired second chemical state. The length of exposure is adjusted, for example, depending on the proportion of degradable crosslinkers of which fragmentation is desired.

In a further embodiment, in addition to using an external energy source, activation of the degradable crosslinkers can occur by catalysis. Catalysis can accelerate the fragmentation rate of the degradable crosslinker and/or lower the activation temperature of the degradable crosslinker. In catalysis, the catalyst does not become incorporated into the degradable crosslinker or fragments therefrom, but merely acts to accelerate the fragmentation of the degradable crosslinker.

In one embodiment where fragmentation of the degradable crosslinker is catalyzed, an acid or base is added to the degradable crosslinker and compositions containing the same. For example, fragmentation of an aldoxime ester into a nitrile and a carboxylic acid can be facilitated by the addition of either an acid or a base. Bases that can be used to initiate acid/base catalyzed fragmentation include, for example, organic bases such as tertiary amines and mixtures thereof. Acids that can be used to initiate this type of fragmentation include, for example, sulfuric acid, p-toluene sulfonic acid, oxalic acid, and mixtures thereof Fragmentation of other degradable crosslinkers can also be initiated in this manner or using other appropriate mechanisms as recognizable to those of ordinary skill in the art. The catalyst can be introduced into the composition in either an active or latent state (e.g., a catalyst that does not become active until irradiated with ultraviolet radiation). Generally, the catalyst is added after polymerization of the polymer in which the degradable crosslinker is incorporated. By adding the catalyst after polymerization, one need not be concerned with activation of the degradable crosslinker prior to, or during, formation of the polymer.

For acid-/base-catalyzed fragmentation, any suitable amount of an acid or base is added to the composition in order to accelerate the fragmentation rate of the degradable crosslinker and/or lower the activation temperature of the degradable crosslinker. Then, the mixture is heated to a temperature sufficient to initiate fragmentation of the degradable crosslinker (i.e., the activation temperature). Typically, the activation temperature is lower than those activation temperatures where catalysis is not used, such as those described above with respect to thermal activation of degradable crosslinkers.

Advantageously, degradable crosslinkers fragment, upon activation, into at least two fragments (i.e., those fragments that remain incorporated as pendant moieties on the polymer in which the degradable crosslinker was incorporated) that are essentially free of free radicals and ethylenic unsaturation. Therefore, compositions containing the degradable crosslinkers are relatively stable after transformation to their altered chemical state, as compared to, for example, the compositions of Hendry et al. that contain polymers having fragments containing free radicals or ethylenic unsaturation, both of which are susceptible to recombination or degradation.

Any suitable chemistry can be used for the degradable crosslinker so long as the crosslinker contains at least one energetically labile moiety (i.e., a moiety that fragments upon activation by an external energy source). A degradable crosslinker may contain more than one energetically labile moiety. The energetically labile moieties may or may not be the same throughout the degradable crosslinker.

According to the invention, the fragments that remain incorporated as pendant moieties on the polymer in which the degradable crosslinker was incorporated are essentially free of free radicals and ethylenic unsaturation. Suitable degradable crosslinker chemistries for achieving this advantage include, for example, those containing esters, particularly those containing the following esters and carbonates: aldoxime esters, aldoxime carbonates, amide esters, and mixtures thereof.

Mixtures of various degradable crosslinkers can be used in accordance with the present invention. For example, if a multiple-tier degradation is desired, a mixture of different thermally degradable crosslinkers may be useful. That is, some of the crosslinkers may fragment at lower temperatures than other degradable crosslinkers in the composition. Furthermore, a mixture of degradable crosslinkers that fragment when subjected to different external energy sources (e.g., a mixture containing at least one thermally degradable crosslinker and at least one degradable crosslinker that fragments upon exposure to ultraviolet radiation) can be used in compositions of the invention. The crosslinkers can then be degraded in a stepwise manner, if desired, providing intermediate compositions having increasingly lower levels of crosslinking density and, thus, increasingly different chemical states.

Furthermore, a mixture of degradable crosslinkers and conventional (i.e., non-degradable) crosslinkers may also be used. That is, the degradable crosslinkers as defined in the present invention would contain energetically labile moieties. Conventional crosslinkers, which include all crosslinkers that do not meet the requirements of the present invention, may or may not contain energetically labile moieties. For example, the conventional crosslinkers described by Hendry et al. (U.S. Pat. No. 3,909,497) and thermally reversible crosslinkers (e.g., ionic or physical crosslinkers) may be used in conjunction with degradable crosslinkers of the invention. Compositions containing the crosslinkers could be subjected to an external energy source to activate the degradable crosslinkers, causing fragmentation of all, or a portion, of the degradable crosslinkers. In any event, in certain embodiments, the remaining composition still retains some degree of crosslinking, which is imparted by the conventional crosslinkers.

Each degradable crosslinker typically contains at least two free radically polymerizable groups (e.g., ethylenically unsaturated groups) when the degradable crosslinker is used to crosslink polymer compositions. The free radically polymerizable groups are generally copolymerizable with monomers used to prepare the polymers in the composition. Preferably, the free radically polymerizable groups are part of (meth)acrylate moieties in the degradable crosslinker. By using (meth)acrylate degradable crosslinkers, incorporation of the degradable crosslinkers into (meth)acrylate polymers is facilitated. That is, (meth)acrylate degradable crosslinkers have similar polymerization reactivities as (meth)acrylate monomers, with which they may be copolymerized.

The presence of the free radically polymerizable groups facilitates incorporation of the degradable crosslinker into a polymer during polymerization. By incorporating the degradable crosslinker into the polymer, crosslinking of the polymer results. As free radical polymerization is the preferred polymerization method, the degradable crosslinker preferably does not contain any groups that interfere with (i.e., slow the rate of, or prevent any) free radical polymerization.

The degradable crosslinkers are further described below, with reference to certain terms understood by those in the chemical arts as referring to certain hydrocarbon groups. Such hydrocarbon groups, as used herein, may include one or more heteroatoms (e.g., oxygen, nitrogen, sulfur, or halogen atoms), as well as functional groups (e.g., oxime, ester, carbonate, amide, ether, urethane, urea, carbonyl groups, or mixtures thereof). Depending on the chemistry, the functional groups may also be degradable according to the present invention.

The term "aliphatic group" means a saturated or unsaturated, linear, branched, or cyclic hydrocarbon group. This term is used to encompass, alkyl, cycloalkyl, alkylene (e.g., thioalkylene and oxyalkylene), alkenylene, alkenyl, cycloalkenyl, aralkylene, aralkenylene, cycloalkylene, and cycloalkenylene groups, for example.

The term "alkyl group" means a saturated, linear or branched, monovalent hydrocarbon group (e.g., a methyl, ethyl, isopropyl, t-butyl, heptyl, dodecyl, octadecyl, amyl, or 2-ethylhexyl group, and the like).

The term "cycloalkyl group" means a saturated, cyclic, monovalent hydrocarbon group.

The term "alkylene group" means a saturated, linear or branched, divalent hydrocarbon group. Examples of particular alkylene groups are thioalkylene and oxyalkylene groups.

The term "thioalkylene group" means a saturated, linear or branched, divalent hydrocarbon group with a terminal sulfur atom.

The term "oxyalkylene group" means a saturated, linear or branched, divalent hydrocarbon group with a terminal oxygen atom.

The term "alkenylene group" means an unsaturated, linear or branched, divalent hydrocarbon group with one or more carbon-carbon double bonds.

The term "alkenyl group" means an unsaturated, linear or branched, monovalent hydrocarbon group with one or more carbon-carbon double bonds (e.g., a vinyl group).

The term "cycloalkenyl group" means an unsaturated, cyclic, monovalent hydrocarbon group with one or more carbon-carbon double bonds.

The term "aralkylene group" means a saturated, linear or branched, divalent hydrocarbon group containing at least one aromatic group.

The term "aralkenylene group" means an unsaturated, linear or branched, divalent hydrocarbon group containing at least one aromatic group and one or more carbon-carbon double bonds.

The term "cycloalkylene group" means a saturated, linear or branched, divalent hydrocarbon group containing at least one cyclic group.

The term "cycloalkenylene group" means an unsaturated, linear or branched, divalent hydrocarbon group containing at least one saturated or unsaturated cyclic group and at least one carbon-carbon double bond.

The term "aromatic group" means a mononuclear aromatic hydrocarbon group or polynuclear aromatic hydrocarbon group. The term includes both aryl groups and arylene groups.

The term "aryl group" means a monovalent aromatic group.

The term "arylene group" means a divalent aromatic group.

Oxime Esters and Oxime Carbonates

Any suitable oxime ester or oxime carbonate can be used so long as it meets the definition of degradable crosslinkers of the invention. Most preferred are degradable crosslinkers containing at least one aldoxime ester moiety, aldoxime carbonate moiety, or mixtures thereof. Aldoxime esters and aldoxime carbonates were found to be more readily thermally degradable as compared to oxime esters and aldoxime carbonates in general.

Aldoxime esters (including, for example, aldoxime esters and aldoxime thioic esters) and aldoxime carbonates (including, for example, aldoxime carbonates, aldoxime xanthates, and aldoxime trithiocarbonates) generally disassociate into a nitrile fragment and an acid fragment and generally conform to the following structure (I):

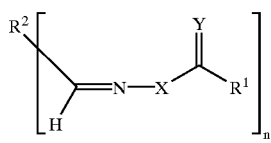

(I)

$R^1$ is a moiety that contains a free radically polymerizable group (e.g., a (meth)acrylate, (meth)acrylamide, styrene, vinyl ester, or fumarate group). For example, $R^1$ can comprise an alkylene, thioalkylene, oxyalkylene, alkenylene, alkenyl, cycloalkenyl, aralkylene, cycloalkylene, aralkenylene, cycloalkenylene, or arylene group linked to the carbonyl group (including thiocarbonyl group) of the ester or carbonate. When $R^1$ comprises, for example, an oxyalkylene or thioalkylene group linked to the carbonyl group (including thiocarbonyl group, if Y is a sulfur atom) through its respective terminal oxygen or sulfur atom, the degradable crosslinker is an oxime carbonate (including thiocarbonates if Y is a sulfur atom). The $R^1$ moiety may also be substituted with one or more heteroatoms (e.g., O, S, N, halogens, etc.) or functional groups (e.g., oximes, esters, carbonates, amides, ethers, urethanes, ureas, carbonyl groups, or mixtures thereof) in the hydrocarbon chain that are inert to free radical polymerization. The acid corresponding to $R^1$ (i.e., $R^1C(Y)XH$) preferably has a $pK_a$ value of greater than one for increased storage stability.

$R^2$ is a moiety that may or may not contain a free radically polymerizable group (e.g., a (meth)acrylate, (meth)acrylamide, styrene, vinyl ester, or fumarate group). Typically, $R^2$ comprises a hydrocarbon group linked to the carbon atom of the aldoxime by a carbon atom. For example, $R^2$ can comprise an alkylene, cycloalkenyl, alkenyl, alkenylene, aralkylene, aralkenylene, cycloalkylene, cycloalkenylene, or arylene group linked to the carbonyl group (including thiocarbonyl group) of the ester or carbonate. The $R^2$ moiety may also be substituted with one or more heteroatoms (e.g., O, S, N, halogens, etc.) or functional groups (e.g., oximes, esters, carbonates, amides, ethers, urethanes, ureas, carbonyl groups, or mixtures thereof) in the hydrocarbon chain that are inert to free radical polymerization.

X and Y are independently selected from oxygen (O) and sulfur (S), depending on the type of aldoxime ester or aldoxime carbonate.

The following examples are provided based on the assumption that $R^1$ is linked to the carbonyl (or thiocarbonyl) group of the ester (or carbonate) by a carbon atom. If $R^1$ terminates in an oxygen or sulfur atom, however, nomenclature would be adjusted as understood by those of ordinary skill in the art. When X is oxygen and Y is oxygen, the aldoxime ester is an aldoxime ester. When X is sulfur and Y is oxygen, the aldoxime ester is an aldoxime thioic S-ester. When X is oxygen and Y is sulfur, the aldoxime ester is an aldoxime thioic O-ester. When X and Y are both sulfur, the aldoxime ester is an aldoxime thioic ester.

The subscript "n" is an integer of one or greater. When n is one, $R^2$ contains a free radically polymerizable group. When n is greater than one, $R^2$ may or may not contain a free radically polymerizable group.

Particularly preferred aldoxime esters and carbonates in the class include those where $R^1$ is independently selected from the following moieties:

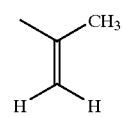

and

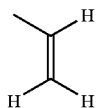

and those where $R^2$ is independently selected from the following moieties:

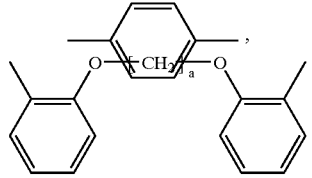

where a is 3, 4, 5, or 6,

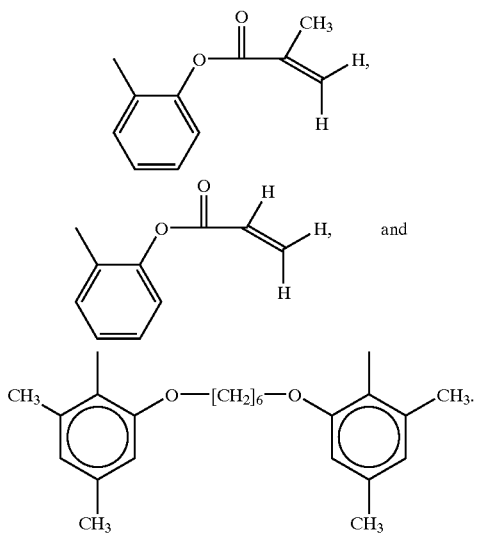

Further preferred embodiments of degradable crosslinkers of the invention are those where n is 2 and $R^1$ is selected from:

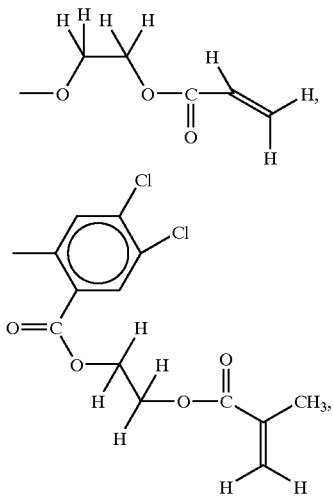

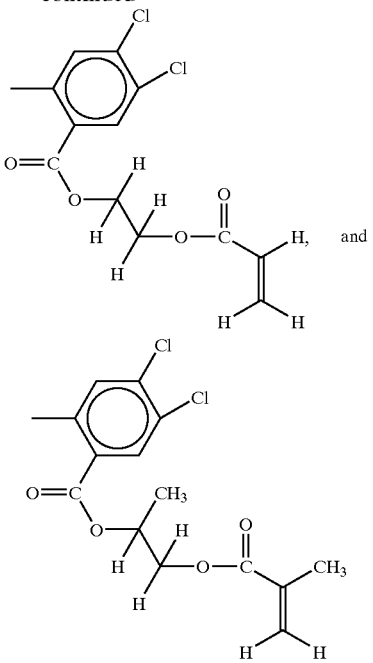

and $R^2$ is:

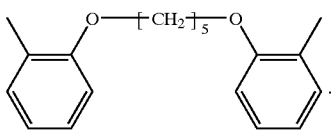

The aldoxime esters and carbonates can be prepared using any suitable method as recognizable to those of ordinary skill in the art. Aldehydes are a general starting material for preparation of the aldoxime esters and carbonates. For example, difunctional (meth)acrylate (i.e., methacrylate or acrylate) aldoxime esters and carbonates can be prepared from diethers of salicylaldehyde. The aldehyde either contains a free radically polymerizable group or is linked to a free radically polymerizable group through a functional group in the aldehyde. During preparation of the aldoxime esters and carbonates, aldehydes are converted to aldoximes with hydroxylamine.

The aldoximes are generally esterified with an acid chloride containing a free radically polymerizable group to make aldoxime esters. Those of ordinary skill in the art will understand that the reactants and/or reaction sequence can be varied to arrive at the same products.

Alternatively, when making aldoxime carbonates, the aldoxime is reacted with a phosgene instead of esterifying the aldoxime. The reaction product is then further reacted with an alcohol to form an aldoxime carbonate. Alternatively, the aldoxime is reacted with a chloroformate instead of esterifying the aldoxime to arrive at an aldoxime carbonate. Again, those of ordinary skill in the art will understand that the reactants and/or reaction sequence can be varied to arrive at the same products.

Subsequent reaction with multifunctional ethylenically unsaturated compounds, such as (meth)acryloyl chlorides, to impart additional free radically polymerizable groups to the aldoxime ester or carbonate, may then be performed, if desired. Specific preparation examples are provided in the Examples section, infra.

Amide Esters

An amide ester, as used herein, is a compound containing at least one amide group and at least one ester group. Amide esters (including, for example, amide esters, amide thioic esters, and amide dithioic esters) generally cyclize to an imide, eliminating an alcohol or thiol and generally conform to the following structure (II):

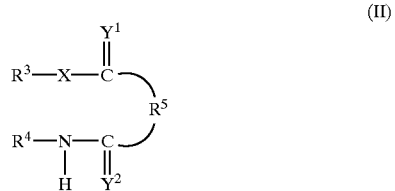

(II)

$R^3$ is a moiety that contains a free radically polymerizable group (e.g., a (meth)acrylate, (meth)acrylamide, styrene, vinyl ester, or fumarate group) and links to the oxygen atom of the ester (if X and $Y^1$ are both oxygen) or thioic O-ester (if X is oxygen and $Y^1$ is sulfur), or links to the sulfur atom of the thioic S-ester (if X is sulfur and $Y^1$ is oxygen) or dithioic ester (if X and $Y^1$ are both sulfur). For example, $R^3$ can comprise an alkenylene, alkenyl, cycloalkenyl, alkylene, aralkylene, aralkenylene, cycloalkylene, cycloalkenylene, or arylene group linked to the oxygen atom of the ester (if X and $Y^1$ are both oxygen), thioic O-ester (if X is oxygen and $Y^1$ is sulfur), thioic S-ester (if X is sulfur and $Y^1$ is oxygen), or dithioic ester (if X and $Y^1$ are both sulfur). The $R^3$ moiety may also be substituted with one or more heteroatoms (e.g., O, S, N, halogens, etc.) or functional groups in the hydrocarbon chain (e.g., oximes, esters, carbonates, amides, ethers, urethanes, ureas, carbonyl groups, or mixtures thereof) that are inert to free radical polymerization.

$R^4$ is a moiety that may or may not contain a free radically polymerizable group (e.g., a (meth)acrylate, (meth)acrylamide, styrene, vinyl ester, or fumarate group). For example, $R^4$ can comprise any hydrocarbon group linked to the nitrogen atom of the amide by a carbon atom. For example, $R^4$ can comprise an alkyl, cycloalkyl, alkylene, thioalkylene, oxyalkylene, alkenylene, alkenyl, cycloalkenyl, aralkylene, aralkenylene, cycloalkylene, cycloalkenylene, aryl, or arylene group linked to the nitrogen atom of the amide. The $R^4$ moiety may also be substituted with one or more heteroatoms (e.g., O, S, N, halogens, etc.) or functional groups (e.g., oximes, esters, carbonates, amides, ethers, urethanes, ureas, carbonyl groups, or mixtures thereof) in the hydrocarbon chain that are inert to free radical polymerization.

$R^5$ is a moiety that links to the amide carbonyl (if $Y^1$ is oxygen) or amide thiocarbonyl (if $Y^2$ is sulfur) with at least one carbon atom and to the ester carbonyl (if $Y^1$ is oxygen) or ester thiocarbonyl (if $Y^2$ is sulfur) with at least one carbon atom. $R^5$ may or may not contain a free radically polymerizable group (e.g., a (meth)acrylate, (meth)acrylamide, styrene, vinyl ester, or fumarate group). However, one, but not both, of $R^4$ or $R^5$ contains a free radically polymerizable group. Examples of $R^5$ include those moieties capable of becoming incorporated into a 5- or 6-membered ring, which ring includes $R^5$ and the imide, upon cyclization of the degradable crosslinker to an imide. As such, typically $R^5$ contains two or three atoms in a chain, with the terminal atoms each being carbon. When there are three atoms in the chain, the center atom may be, for example, carbon or a divalent heteroatom (e.g., oxygen or sulfur). The chain may also contain pendent hydrocarbon groups therefrom, such as when $R^5$ contains a free radically polymerizable group. One or more atoms in the chain may also be part of a ring structure. Preferably, $R^5$ comprises an alkylene or arylene (e.g., ortho arylene) group.

X, $Y^1$, and $Y^2$ are independently selected from oxygen (O) and sulfur (S), depending on the type of amide ester. That is, each Y constituent ($Y^1$ and $Y^2$) occurring within an amide ester may be the same or different from other Y constituents. Similarly, X may be the same as one or both of the Y constituents. Alternatively, X may be different from each of the Y constituents.

When X is oxygen, $Y^1$ is oxygen, and $Y^2$ is oxygen, the amide ester is an amide ester. When X is oxygen, $Y^1$ is oxygen, and $Y^2$ is sulfur, the amide ester is a thioamide ester. When X is oxygen, $Y^1$ is sulfur, and $Y^2$ is oxygen, the amide ester is an amide thioic O-ester. When X is oxygen, $Y^1$ is sulfur, and $Y^2$ is sulfur, the amide ester is a thioamide thioic O-ester.

When X is sulfur, $Y^1$ is sulfur, and $Y^2$ is sulfur, the amide ester is a thioamide dithioic ester. When X is sulfur, $Y^1$ is oxygen, and $Y^2$ is sulfur, the amide ester is a thioamide thioic S-ester. When X is sulfur, $Y^1$ is sulfur, and $Y^2$ is oxygen, the amide ester is an amide dithioic ester. When X is sulfur, $Y^1$ is oxygen, and $Y^2$ is oxygen, the amide ester is an amide thioic S-ester.

Particularly preferred amide esters in the class include those where $R^3$ is:

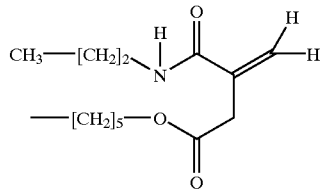

$R^4$ is:

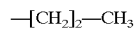

and $R^5$ is:

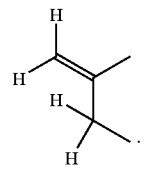

The amide esters can be prepared using any suitable method as recognizable to those of ordinary skill in the art. Anhydrides are a general starting material for preparation of the amide esters. The anhydride is generally combined with a free radically polymerizable alcohol to form an ester acid. The acid moiety is then converted to a more chemically reactive derivative, such as an acid chloride, that can react with a primary amine, such as an amino alcohol or diamine. Upon reaction with the primary amine, an amide ester is formed. Subsequent reaction with multifunctional ethylenically unsaturated compounds, such as (meth)acryloyl chlorides, to impart additional free radically polymerizable groups to the amide ester may then be performed, if desired. Those of ordinary skill in the art will understand that the reactants and/or reaction sequence can be varied to arrive at the same products. Specific preparation examples are provided in the Examples section, infra.

Preparation of Crosslinked Polymer Compositions Comprising the Degradable Crosslinker The degradable crosslinkers can be used in a wide variety of polymers. Depending on the amounts and types of components in the crosslinked polymer compositions, the crosslinked polymer compositions can be tacky to the touch or essentially non-tacky to the touch at room temperature.

Generally, the degradable crosslinker is copolymerized with the monomer component (i.e., one or more monomers that are copolymerizable with the degradable crosslinker) used to prepare the polymers. The monomer component and degradable crosslinker are copolymerized according to any suitable method, as recognizable to those of ordinary skill in the art.

Any suitable monomer, or combination thereof, may be used. Preferably, monomers of the present invention are ethylenically unsaturated monomers, preferably monoethylenically unsaturated monomers, such that they can be copolymerized with the degradable crosslinkers. Preferably, the monomers are selected from (meth)acrylates, (meth)acrylic acids, vinyl esters, (meth)acrylamides, and combinations thereof.

Particularly preferred monomers are (meth)acrylate monomers, including monoethylenically unsaturated monomers, such as (meth)acrylate esters of non-tertiary alkyl alcohols, the alkyl groups of which comprise from about 1 to about 18 carbon atoms, preferably about 4 to about 12 carbon atoms, and mixtures thereof Examples of suitable (meth)acrylate monomers useful in the present invention include, but are not limited to, methylacrylate, ethylacrylate, methyl methacrylate, ethyl methacrylate, n-butyl acrylate, decyl acrylate, 2-ethylhexyl acrylate, 2-ethylhexyl methacrylate, hexyl acrylate, isoamyl acrylate, isodecyl acrylate, isodecyl methacrylate, isononyl acrylate, isooctyl acrylate, lauryl acrylate, 2-methyl butyl acrylate, 4-methyl-2-pentyl acrylate, ethoxyethoxyethyl acrylate, isobornyl acrylate, isobornyl methacrylate, 4-t-butylcyclohexyl methacrylate, cyclohexyl methacrylate, phenyl acrylate, phenylmethacrylate, 2-naphthyl acrylate, 2-naphthyl methacrylate, and mixtures thereof. Particularly preferred are 2-ethylhexyl acrylate, isooctyl acrylate, lauryl acrylate, n-butyl acrylate, ethoxyethoxyethyl acrylate, and mixtures thereof.

Examples of other ethylenically unsaturated monomers include, but are not limited to, vinyl esters (e.g., vinyl acetate, vinyl pivalate, and vinyl neononanoate); vinyl amides; N-vinyl lactams (e.g., N-vinyl pyrrolidone and N-vinyl caprolactam); (meth)acrylamides (e.g., N,N-dimethyl acrylamide, N,N-dimethyl methacrylamide, N,N-diethyl acrylamide, and N,N-diethyl methacrylamide); (meth)acrylonitrile; -maleic anhydride; styrene and substituted styrene derivatives (e.g., α-methyl styrene); and mixtures thereof.

Optional acidic monomers may also be used. Useful acidic monomers include, but are not limited to, those selected from ethylenically unsaturated carboxylic acids, ethylenically unsaturated sulfonic acids, ethylenically unsaturated phosphonic acids, and mixtures thereof Examples of such compounds include those selected from acrylic acid, methacrylic acid, itaconic acid, fumaric acid, crotonic acid, citraconic acid, maleic acid, β-carboxyethyl acrylate, 2-sulfoethyl methacrylate, styrene sulfonic acid, 2-acrylamido-2-methylpropane sulfonic acid, vinyl phosphonic acid, and the like, and mixtures thereof.

The following polymerization techniques, which are described infra, can be used for polymerizing the monomer component and degradable crosslinker. These techniques include, but are not limited to: the conventional techniques of solvent polymerization, dispersion polymerization, emulsion polymerization, suspension polymerization, solventless bulk polymerization, and radiation polymerization, including processes using ultraviolet light, electron beam, and gamma radiation. The starting materials may comprise any suitable additives, such as a polymerization initiator, especially a thermal initiator or a photoinitiator, of a type and in an amount effective to polymerize the monomers and degradable crosslinker.

When polymerized using emulsion, suspension, or dispersion polymerization, the resulting crosslinked polymer compositions are advantageously capable of being readily made into storage-stable, free-flowing polymer compositions. "Free-flowing" polymer compositions are those compositions containing a multitude of solid state particulates that do not substantially agglomerate (i.e., the particulates are capable of being moved by gravitational forces alone) at temperatures below the activation temperature of the degradable crosslinkers. Preferably, the free-flowing polymer compositions do not substantially agglomerate at the storage temperature and pressure.

The free-flowing polymer compositions are especially useful in certain feeding, blending, and delivery methods. For example, free-flowing polymer compositions facilitate feeding hot-melt coating compositions. Conventional feeding equipment, such as hopper feeders and powder conveyers, can be used with free-flowing polymer compositions of the invention. Furthermore, shipping and handling of free-flowing polymer compositions is typically less expensive and more convenient than shipping and handling associated with bulk polymer compositions. Free-flowing polymer compositions can also be easily dry-blended, without the need for solvents or melt blending.

The free-flowing polymer compositions can be prepared using any suitable method. In one embodiment, the particulates are filtered to a dryness of about 75% to about 95% solids using any suitable filtering technique, such as using a NÜTSCHE filter (commercially available from Northland Stainless, Inc.; Tomahawk, Wis.). The filtered particulates are then blended with silica (such as that commercially available from Degussa Corporation; Ridgefield Park, N.J., under the trade designation, AEROSIL R-972), using any suitable blending technique, such as using a ribbon blender. The coated particulates are then dried using any suitable technique. For example, the coated particulates can be air-dried in an oven. The coated particulates can also be air-dried in a fluid bed dryer, such as those commercially available from Glatt Air Techniques Inc.; Ramsey, N.J.

Solvent Polymerization Method

Solvent polymerization is well known in the art and described in various sources such as U.S. Pat. No. Re 24,906 (Ulrich) and U.S. Pat. No. 4,554,324 (Husman et al.). Briefly, the procedure is carried out by adding the monomers, degradable crosslinker, a suitable solvent such as ethyl acetate, and an optional chain transfer agent to a reaction vessel. Then, a free radical initiator is added to the mixture. Many suitable free radical initiators are commercially available, such as those available from E. I. duPont de Nemours & Company; Wilmington, Del. under the VAZO trade designation. Specific examples include VAZO 64 and VAZO 52, which are described below in the Table of Abbreviations. Suitable initiators also include hydroperoxides, such as tert-butyl hydroperoxide, and peroxides, such as benzoyl peroxide and cyclohexane peroxide.

After purging with nitrogen, the reaction vessel is maintained at an elevated temperature, typically in the range of about 40° C. to about 100° C., until the reaction is complete. Typically, the reaction takes about one to about twenty hours to complete, depending on the batch size and reaction temperature.

Dispersion Polymerization Method

Dispersion polymerization typically is carried out as single-phase reaction of a mixture consisting of a solution of monomers, degradable crosslinker, initiator, and steric stabilizer in a solvent that does not dissolve the resulting polymer. The initial stage of the polymerization is a typical solution polymerization and the polymer chains grow in size until they become insoluble in the reaction mixture. As the polymer starts to precipitate out of the mixture, the steric stabilizer adsorbs on the surface of the polymer, preventing coalescence of the polymer particles as they form. The reaction will continue until all of the monomer is consumed, resulting in the formation of crosslinked polymer particles that are insoluble in the reaction medium in which they are formed.

Emulsion Polymerization Method

Emulsion polymerization is also described in U.S. Pat. No. Re 24,906 (Ulrich). For example, the monomers are mixed with the degradable crosslinker, distilled water, an emulsifying agent, and suitable initiators in a reaction vessel. Then, the reaction vessel is purged with nitrogen and heated, with agitation, to a temperature in the range of about 25° C. to about 80° C., until the reaction is complete.

For ease of handling and/or to employ emulsion-polymerized polymers as powders, the emulsion-polymerized polymer is typically spray-dried using conventional drying techniques. To prepare such powders, the emulsion-polymerized base copolymer can be fed to a nozzle that sprays the emulsion into a stream of hot gas. The aqueous emulsion medium evaporates first, forming a small droplet of concentrated polymer. As aqueous medium removal nears completion, the droplet is transformed into a powder particle or clusters thereof See, for example, U.S. Pat. No. 3,772,262 (Clementi) and K. Masters, "Spray Drying," 2nd ed., Wiley: 1976.

Suspension Polymerization Method

Crosslinked polymer compositions can also be prepared in bead form using suspension polymerization methods. Such suspension methods are described, for example, in European Patent Application Number 0 853 092 (Minnesota Mining and Manufacturing Co.). This suspension process involves mixing the monomers, degradable crosslinker, free radical initiator, chain transfer agent, and other desired additives to form a premix. A suspension stabilizer, such as dextrin or a dextrin derivative, is combined with water and then with the premix to form an oil-in-water suspension. The resulting suspension typically comprises from about 10 to about 50 weight percent premix and from about 90 to about 50 weight percent water phase.

Polymerization is then initiated, typically thermally, and carried out for about two to about sixteen hours at a temperature of about 40° C. to about 90° C. The crosslinked polymer beads can be isolated by a variety of means and generally have a diameter of one to 5,000 micrometers. Similar to the emulsion process, smaller suspension-polymerized particles may also be capable of being spray-dried to recover the polymer. Larger particles may be capable of being isolated, for example, by simple filtration and air-drying.

In certain embodiments, after isolating from suspension and drying, the suspension beads can show some blocking resulting from tackiness of the suspension beads. Due to this blocking, the suspension beads can partially, or even completely, lose desired free-flowing characteristics. To prevent this loss of flow, a dusting agent, such as hydrophobic silica (e.g., AEROSIL R-972, commercially available from Degussa Corporation; Ridgefield Park, N.J.), can be added immediately after isolating the beads. When treated in this manner, suspension beads can also be used in processing methods and delivery techniques that advantageously exploit the powder-like nature of these materials.

Solventless Polymerization Method

Solventless polymerization methods, such as the methods described for polymerizing packaged polymerizable compositions in U.S. Pat. No. 5,804,610 (Hamer et al.), may also be utilized to prepare the crosslinked polymer compositions. In one embodiment, from about 0.1 to about 500 grams of a polymerizable mixture comprising monomers, degradable crosslinker, initiator, and optional chain transfer agent is completely surrounded by a packaging material. In another preferred embodiment, the polymerizable mixture is disposed on the surface of a sheet, or between a pair of two substantially parallel sheets, of the packaging material.

The packaging material is made of a material that, when combined with the resulting polymer, does not substantially adversely affect the desired polymer characteristics. The packaging material should be appropriate for the polymerization method used. For example, with photopolymerization, it is necessary to use a film material that is sufficiently transparent to ultraviolet radiation at the wavelengths necessary to effect polymerization. Polymerization can be effected by exposure to ultraviolet (UV) radiation as described in U.S. Pat. No. 4,181,752 (Martens et al.). In a preferred embodiment, the polymerization is carried out with UV black lights having over 60 percent, and preferably over 75 percent, of their emission spectra between about 280 to about 400 nanometers (nm), with an intensity between about 0.1 to about 25 mW/cm$^2$.

In another solventless polymerization method, crosslinked polymer compositions of the present invention are prepared by photoinitiated polymerization methods according to the technique described, for example, in U.S. Pat. No. 4,181,752 (Martens et al.). For example, the monomers and photoinitiator can be mixed together in the absence of solvent and partially polymerized to make a coatable syrup. Coatable syrups generally have a viscosity in the range of from about 500 centiPoise to about 50,000 centiPoise. In yet another way, the monomers can be mixed with a thixotropic agent, such as fumed hydrophilic silica, to achieve a thickened monomer mixture having a coatable thickness. The degradable crosslinker and any other ingredients are then added to the prepolymerized syrup or thickened monomer mixture. Alternatively, these other ingredients (preferably, with the exception of the degradable crosslinker) can be mixed with the monomers prior to partial polymerization or thickening of the monomer mixture.

The resulting polymerizable composition is coated onto a substrate (which may be transparent to UV radiation) and polymerized in an inert atmosphere (i.e., an oxygen-free, such as nitrogen, atmosphere) by exposure to UV radiation. A sufficiently inert atmosphere can also be achieved by covering a layer of the polymerizable coating with a plastic film that is substantially transparent to UV radiation and irradiating through that film, as described in U.S. Pat. No. 4,181,752 (martens et al.), using a UV light source. Alternatively, instead of covering the polymerizable coating, an oxidizable tin compound may be added to the polymerizable composition to increase the tolerance of the composition to oxygen, as described in U.S. Pat. No. 4,303,485 (Levens). The UV light source preferably has 90% of the emissions between about 280 and about 400 nanometers (more preferably between about 300 and about 400 nanometers), with a maximum emission at about 350 nanometers.

Additives

A wide variety of conventional additives can be mixed with the crosslinked polymer composition. In fact, when the crosslinked polymer composition is essentially non-tacky at room temperature, blending of additives with the crosslinked polymer composition is often easier. The components (i.e., crosslinked polymer composition and additives) are even able to be dry-blended, as opposed to the more costly and complicated melt-blending techniques.

Any suitable additive can be blended with the crosslinked polymer composition. For certain applications, expandable microspheres, glass bubbles, and chemical blowing agents may be useful additives. Those of ordinary skill in the art will recognize a wide variety of additives that may be useful when preparing crosslinked polymer compositions of the invention for specific applications.

For example, tackifiers can be added to the crosslinked polymer composition to increase the composition's tack. Plasticizers can also be added to the crosslinked polymer composition. For example, when the polymer is derived from a high proportion of relatively high glass transition temperature (Tg) monomers, addition of a plasticizer can increase the tack of the composition.

If an increase in crosslink density of the composition is desired at any time after fragmentation of at least a portion of the degradable crosslinkers, crosslinking additives may be added to the composition. For example, ultraviolet (UV) crosslinkers facilitate crosslinking by exposure to ultraviolet radiation. Thermally reversible crosslinkers, such as those described in PCT Publication Number WO 99/42,536 (Minnesota Mining and Manufacturing Co.), facilitate crosslinking without requiring an external energy source, such as radiation.

If the crosslinked polymer composition is tacky to the touch at ambient temperature and pressure, it may be desirable to use a coating agent, such as the shell materials described in U.S. Pat. No. 5,322,731 (Callahan, Jr. et al.), or a dusting agent, such as hydrophobic silica or the like, in order to facilitate easier handling of the crosslinked polymer compositions prior to their application to a substrate. Preferably, when using a coating agent or dusting agent for this purpose, the amount of the coating/dusting agent used is an effective amount to render the composition non-tacky to the touch at ambient temperature and pressure.

Application/Processing of the Crosslinked Polymer Compositions

The crosslinked polymer compositions can be applied to a wide variety of substrates to form a coating thereon. The substrate can take any suitable form, such as, for example, a sheet, a fiber, or a shaped article. The coating thickness will vary depending upon various factors such as, for example, the particular application, the crosslinked polymer composition formulation, and the nature of the substrate (e.g., its absorbency, porosity, surface roughness, amount of creping, chemical composition, etc.). For example, a porous or rough substrate will typically require a thicker coating than less porous or smoother substrates. As another example, pressure-sensitive adhesive coatings typically have a thickness of about 25 microns to about 250 microns.

The method of processing the composition, or applying it to a substrate, will vary depending on the desired use of the composition. In one embodiment, activation of the composition occurs prior to applying the composition to a substrate. In another embodiment, activation of the composition occurs after applying the composition to a substrate. In another embodiment, the composition is activated while it is being applied to a substrate.

To activate the composition (fragmenting at least a portion of the degradable crosslinker, also referred to as "activating the degradable crosslinker" or a similar phrase), an external energy source is applied to at least a portion of the composition. The energy source used to activate the composition can be diffuse, so as to activate broad areas of the composition, or focused, so as to activate discrete, predetermined portions of the composition. Any suitable energy source can be used, such as a thermal source (e.g., oven, infrared radiation lamp or laser, slot burner, or microwave source (when used in conjunction with a receptor for microwave radiation)).

In one embodiment, the external energy source is applied to a discrete portion of the composition, thereby activating the degradable crosslinker in only a portion of the composition. Resulting compositions may, thus, have varying chemical states throughout, depending on whether the degradable crosslinker was activated in that particular portion. In another embodiment, the external energy source is applied to substantially all of the composition, thereby activating the degradable crosslinker in substantially all of the composition. Resulting compositions, thus, having substantially identical chemical properties throughout.

Activation Followed by Application

In certain embodiments, the crosslinked polymer composition is first activated (to fragment at least a portion of the degradable crosslinker) and then applied to a substrate in separate processing steps. That is, the crosslinked polymer composition is first transformed to a composition having reduced crosslink density by fragmenting at least a portion of the degradable crosslinkers incorporated therein. The composition is then applied to a substrate using any suitable method. For example, organic solvent coating and hot-melt coating techniques, which are described infra, may be used.

Any conventional coating technique can be used to apply the compositions to target substrates from organic solvent solutions. Useful coating techniques include brush, roll, spray, spread, wire, gravure, transfer roll, air knife, or doctor blade coating.

Hot-melting coating techniques are also useful. For example, the compositions may be introduced into a vessel to melt and activate the composition. The composition is subjected to a temperature sufficient to melt and activate the composition and thoroughly mix any additional components, after which the composition is coated onto a substrate. This step can be done conveniently in a heated extruder, bulk tank melter, melt-on-demand equipment, or hand-held hot-melt adhesive gun.

The hot-melt compositions can be coated onto a substrate using any suitable method. For example, the compositions can be delivered out of a film die and coated by contacting the drawn hot-melt composition with a moving web (e.g., plastic web) or other suitable substrate. Using this method, the hot-melt material is applied to the moving preformed web using a die having flexible die lips, such as a rotary rod die. A related coating method involves extruding the composition and a coextruded backing material from a film die and cooling the layered product to form a multi-layered construction, such as an adhesive tape. After forming by any of these continuous methods, the resulting films or constructions can be solidified by quenching using both direct methods (e.g., chilled rolls or water baths) and indirect methods (e.g., air or gas impingement).

Activation with Application

In other embodiments, the crosslinked polymer composition is activated (to fragment at least a portion of the degradable crosslinker) while applying the composition to a substrate in essentially a single processing step.

For example, the composition may be activated and applied using a reactive flame spray technique. The flame spray technique is a process whereby the deposition of a largely molten material is enabled by using a highly directional gas stream. Flame spray methods include flame spraying and reactive flame spraying. Flame spraying involves the introduction of a material to be deposited into a flame that is typically generated external to the gas introduction apparatus. The composition is activated while applying it to a substrate by using reactive flame spraying, wherein the composition, which is typically in the form of a powder, is at least partially activated during spraying.

In flame spray techniques, the kinetic energy of the feed gases typically transports the molten material in a transport gas stream. However, an additional transport gas stream may be utilized. The thermal energy in a flame spray system is determined by the flow rates and composition of fuel and oxidizer gases that are used. Flames are typically created from acetylene and oxygen in order to produce a relatively hot flame. Lower temperature systems, for the deposition of thermally sensitive materials, can be provided by using propane/air flames.

All material introduction methods typically have the same ultimate goal—to produce small, potentially liquified particles that collide with the receiving surface. Commercial flame spray systems are available that use either particle or wire feeds. Other systems have been described that utilize liquid feeds (K. A. Gross, et al, *Journal of Thermal Spray Technology*, 8, 583–589 (1999). For example, several flame deposition systems have been reported that describe the spraying of a liquid in, or near, a flame to achieve deposition. Material to be deposited in powder form is typically introduced to a depositing flame in a pressurized transport gas stream. This transport gas stream is typically either the oxidizer for the flame or a designated transport gas stream. Powders can be gravity fed or mechanically fed into the transport gas stream. Alternatively, powders can be drawn into a transport gas stream from a contained, fluidized bed due to the venturi effect of the transport gas stream.

Depositing material typically reaches only a fraction of the flame temperature during the flame residence time. Control of this residence time is a key process variable in flame spray deposition. The precise residence time needed for a given system will be determined by the characteristics of the flame spray system and the depositing material. This residence time can be modified, for example, by changing the flow rate of a designated transport gas stream or by changing the precise point of introduction of the depositing material into the flame.

Depositing material may also be modified by further exposure to the flame. Likewise, a surface to be coated may also be modified, such as by heating with a flame or other thermal source prior to deposition, in order to allow the depositing material to remain in a softened, or fluid, state for a longer time on the receiving surface.

Flames generated in typical flame spray systems are viewed exclusively as sources of thermal energy to provide a phase change of the depositing material, such as from a solid particle to a molten droplet. Accompanying this phase change is a change in the rheological properties of the material. Incidental oxidation of the depositing material may also occur in typical flame spray processes. However, reactive flame spraying utilizes the thermal energy of the flame to fragment at least a portion of the degradable crosslinker, which allows the particles to flow more readily when they impinge the substrate and also increases the pressure-sensitive adhesive tack of the applied composition. This fragmentation is a result of a chemical reaction that occurred due to the thermal energy. That is, a flame spray process that specifically utilizes the flame to fundamentally alter the composition of the injected material is considered reactive flame spraying.

Application Followed by Activation

In yet other embodiments, the crosslinked polymer composition is first applied to a substrate and then activated (to fragment at least a portion of the degradable crosslinker). The composition can be applied to a substrate using any suitable method. For example, aqueous solution coating, aqueous dispersion coating, solventless coating (followed by polymerization), thermal deposition, and powder coating can be used.

Any conventional coating technique can be used to apply the compositions to target substrates from aqueous solutions, including emulsions and dispersions. Useful coating techniques include brush, roll, spray, spread, wire, gravure, transfer roll, air knife, curtain, slurry, or doctor blade coating.

As another example, the composition can be applied to a substrate using the solventless coating and polymerization method described in U.S. Pat. No. 4,181,752 (Martens et al.), supra. In this embodiment, the degradable crosslinker is added to a partially polymerized, or thickened, monomer mixture. The resulting composition is then coated onto a substrate and polymerized. After the composition is polymerized, it is activated.

Yet another example of this embodiment involves thermal deposition of the crosslinked polymer composition. Particles of the composition are coated on a substrate and then heated using a suitable thermal source, such as those described in PCT Publication No. WO 99/03,642 (Minnesota Mining and Manufacturing Co.). Optionally, the substrate on which the heated particles are coated is softened to facilitate adhesion of the particles to the substrate. If softened, the substrate is generally softened by thermal energy or thermal radiation. For example, the substrate can be softened using heat from the same thermal source that is used for coating and heating particles of the composition.

A still further example of Application Followed by Activation involves conventional, as opposed to reactive, flame spraying of the crosslinked polymer composition. The conventional flame spray technique was described above with respect to "Activation with Application."

One of the advantages of using crosslinked polymer compositions of the present invention is the ability to deliver the crosslinked polymer composition using powder coating techniques. In addition to the spray-dried, emulsion-polymerized compositions and the free-flowing, suspension- or dispersion-polymerized particles described above, the crosslinked polymer composition in powdered form can also be prepared using mechanical techniques such as cryo-grinding or hammer milling.

The capability of delivering the crosslinked polymer compositions as powdered coatings offers several advantages and alternatives over crosslinked polymer compositions coated using conventional techniques. For example, when the crosslinked polymer composition is in the form of particulates, the crosslinked particulates can be coated on a substrate in the Z-direction (i.e., the direction perpendicular to the substrate) using powder coating techniques, described infra, and then activated to fragment at least a portion of the degradable crosslinkers. Upon fragmentation, the particulates fuse together to form a continuous coating on the substrate. By applying the crosslinked polymer composition to a substrate in this manner, the resulting coating is less oriented, and thus has reduced stress, as compared to coatings applied by conventional hot-melt coating methods, such as die-extrusion. These process-related effects can compromise the performance of the resulting coatings.

Hot-melt coating also has its limitations when three-dimensional, or rough, surface coverage is desired. Furthermore, hot-melt coating of wide sheets, or substrates, requires bulky and expensive custom coating dies that are not readily available. By using powder coating techniques to coat all or a portion of such substrate surfaces with crosslinked polymer compositions of the present invention, all of these disadvantages associated with hot-melt coated compositions can be avoided.

Yet, another advantage of powder format of the crosslinked polymer composition is the ease of blending the crosslinked polymer composition with other powdered components. The other powdered components may be other crosslinked polymer compositions of the current invention with different chemistries or crosslinking densities. Alternatively, the other powdered components can be other organic (e.g., polymeric materials) or inorganic materials.

Useful techniques for powder coating of the crosslinked polymer compositions include fluidized-bed coating and electrostatic spray processes. In the fluidized-bed coating process, the crosslinked polymer composition is placed in a container having a porous plate as its base. Air is passed through the plate, causing the composition to expand in volume and fluidize. In this state, the composition possesses some of the characteristics of a fluid. A substrate is then heated in an is oven to a temperature above the melting point of the crosslinked polymer composition. The substrate is dipped into the fluidized bed where the fluidized composition melts on the substrate to form a coating. Depending on the rheology and crosslink density of the crosslinked polymer composition, activation will either fuse the coating into a smooth coating or all or part of the particulate nature of the crosslinked polymer composition can be maintained. Alternatively, a cold substrate can be run over a bed of fluidized particles that are tribo-charged and, thus, cling to the substrate. The coated substrate can then be passed through a heated zone, or nip, to fuse the coating.

In the electrostatic spray process, the powdered material is dispersed in an air stream and passed through a corona discharge field where the particles acquire an electrostatic charge. The charged particles are attracted to and deposited on the grounded substrate. The substrate, usually electrostatically coated at room temperature, is then placed in an oven where the powder melts and forms a coating. See for example, *Kirk-Othmer Encyclopedia of Chemical Technology*, 4$^{th}$ Edition, Wiley: 1993, Vol. 6, pages 635–636.

In all embodiments of application/processing of the crosslinked polymer composition, further processing steps may be performed after application and activation of the crosslinked polymer composition. For example, if desired, the activated polymer composition can be recrosslinked at any time after fragmentation of the degradable crosslinker, such as after applying the composition to a substrate. Typically, such "recrosslinking" is accomplished by radiation (e.g., using electron beam or ultraviolet radiation) of the composition or the incorporation of thermally reversible crosslinkers in the composition, such as those described in PCT Publication Number WO 99/42,536 (Minnesota Mining and Manufacturing Co.). A wide variety of other processing steps may also be performed on the resulting polymer compositions.

EXAMPLES

These examples are merely for illustrative purposes only and are not meant to be limiting on the scope of the appended claims. All parts, percentages, ratios, etc. in the examples and the rest of the specification are by weight unless indicated otherwise. All reagents were obtained from Aldrich Chemical Company; Milwaukee, Wis., unless otherwise noted. All solvents were obtained from VWR Scientific; West Chester, Pa., unless otherwise noted.

| Table of Abbreviations | |
|---|---|
| Trade Designation/ Abbreviation | Description |
| AA | acrylic acid |
| ABP | 4-acryloxy benzophenone copolymerizable photocrosslinker derived by reacting equimolar amounts of acryloyl chloride and 4-hydroxy benzophenone |
| AEROSIL R-972 | hydrophobic silica, commercially available from Degussa Corporation; Ridgefield Park, New Jersey |
| DMAEMA | Dimethylaminoethylmethacrylate |
| EHA | 2-ethylhexyl acrylate |
| ESACUR KB-1 | 2,2-dimethoxy-1,2-diphenyl-1-ethanone photoinitiator, commercially available from Sartomer Company; Exton, Pennsylvania |
| HDDA | 1,6-hexanediol diacrylate |
| HDDMA | 1,6-hexanediol dimethacrylate |
| IBA | isobornyl acrylate |
| IOA | isooctyl acrylate, commercially available from NA Industries, Inc.; Chattanooga, Tennessee |
| IOTG | isooctyl thioglycolate chain transfer agent |
| MAA | methacrylic acid |
| MEHQ | 4-methoxyphenol |
| nBA | normal butyl acrylate |
| nOA | normal octyl acrylamide |
| PIC | Polymeric ionic crosslinker, specifically a 40/60 weight ratio of EHA/DMAEMA copolymer, the synthesis of which is described immediately following the test methods below |
| VAZO 52 | azo-bis(2,4-dimethylvaleronitrile) initiator, commercially available from E.I. duPont de Nemours & Co.; Wilmington, Delaware |
| VAZO 64 | azo-bis(isobutyronitrile) initiator, commercially available from E. I. duPont de Nemours & Co.; Wilmington, Delaware |

Test Methods
Gel Test

A polymer was prepared by incorporating the desired amount of a degradable crosslinker into a monomer mixture containing 90 parts of IOA and 10 parts of AA. First, a 90:10 mixture of IOA:AA was prepared and placed in a container with 0.04 part of ESACUR KB-1 per 100 parts IOA:AA. The container was purged with nitrogen and closed. As the nitrogen purging continued, the mixture was irradiated with an ultraviolet (UV) black light (40 Watt UV SYLVANIA BLACKLIGHT, commercially available from Osram Sylvania; Danvers, Mass.) to form a partially polymerized syrup having a coatable Brookfield viscosity estimated to be about 3,000 centiPoise. An additional 0.1 part ESACUR KB-1 and the desired number of parts of the degradable crosslinker were added to the syrup. After mixing, the composition was knife-coated to a thickness of about 50 micrometers between two transparent, siliconized polyester film, each having a thickness of about 37 micrometers.

The laminate was exposed to an UV radiation dosage of about 450 milliJoules per centimeter squared using UV black lights having 90% of the emission spectra between 300 and 400 nanometers, with a maximum emission at about 350 nanometers.

The resulting polymer was then divided into portions. The divided polymer portions were placed on a pre-weighed screen and the liners were removed. The weight of the polymer was obtained.

Then, the polymer was exposed to heat at a specific temperature for a specified amount of time. The temperature was typically 175° C. for 0, 1, 5 and 15 minutes, but the exact time and temperature is specified for each test.

The polymer and screen were placed in a jar containing ethyl acetate and allowed to soak for 24 hours. After soaking, any remaining polymer was removed from the screen and dried at 65° C. for 20 minutes. After drying, the sample was again weighed to obtain the weight of the polymer that remained on the screen. The percent gel is calculated as the ratio of the weight of polymer remaining on the screen after soaking as compared to the original weight of polymer, multiplied by 100.

Tape Tests

The following test methods were used to characterize pressure-sensitive adhesive compositions produced in the following examples:

180° Peel Adhesion

This test is similar to the test method described in ASTM D 3330-90, substituting a glass substrate for the stainless steel substrate described in the test. For the present purpose, this test is also referred to as the "glass substrate peel adhesion test."

Adhesive coatings, having a thickness as indicated in the particular example, on polyester film were cut into 1.27 centimeter by 15 centimeter strips. Each strip was then adhered to a 10 centimeter by 20 centimeter clean, solvent-washed, glass coupon using a 2-kilogram roller passed once over the strip. The bonded assembly dwelled at room temperature for about one minute.

The bonded assembly was then tested for 180° peel adhesion using an IMASS SLIP/PEEL TESTER (Model Number 3M90, commercially available from Instrumentors Inc.; Strongsville, Ohio) at a rate of 2.3 meters per minute (90 inches per minute) over a five second data collection time. Two samples of each composition were tested. The reported peel adhesion value is an average of the peel adhesion value obtained from testing each of the two samples.

Shear Strength

This test is similar to the test method described in ASTM D 3654-88. Adhesive coatings, having a thickness as indicated in the particular example, on polyester film were cut into 1.27 centimeter by 15 centimeter strips. Each strip was then adhered to a stainless steel panel such that a 1.27 centimeter by 1.27 centimeter portion of each strip was in firm contact with the panel, with one end portion of the strip hanging free. The panel with the strip attached was held in a rack such that the panel formed an angle of 178° with the extended strip free end that was tensioned by application of a force of one kilogram applied as a hanging weight from the free end of the strip. The 2° less than 180° was used to negate any peel forces, thus ensuring that only shear strength forces were measured, in an attempt to more accurately determine the holding power of the tape being tested.

The time elapsed for each sample to separate from the test panel was recorded as the shear strength. Failures were noted as adhesive (denoted A, no residue on panel) or cohesive (denoted C, adhesive failed internally with adhesive residue remaining on both the backing and panel). Each test was terminated at 10,000 minutes, unless the adhesive failed at an earlier time (as noted).

Synthesis of PIC

In a glass bottle, 80 grams of EHA, 120 grams of DMAEMA, and 300 grams of ethyl acetate were mixed. To this mixture, 0.6 gram of VAZO 64 was added. The bottle was then made inert with nitrogen gas and sealed. The sealed bottle was tumbled in a 55° C. water bath for 24 hours. The resultant polymer was coated on a siliconized polyester release liner and oven dried for 15 minutes at 65° C. to recover the dried polymer.

EXAMPLES 1–15

Synthesis of Aldoxime Esters

Example 1

Step I

Synthesis of 2-(5-[2-(hydroxyiminomethyl)phenoxy] pentyloxy)benzaldehyde oxime

In a flask equipped with a stirrer, nitrogen inlet, reflux condenser, and addition funnel, 1,350 grams of ethanol and 113 grams of potassium hydroxide were placed. The mixture was stirred until all of the potassium hydroxide dissolved.

To this stirred mixture, 208 grams of salicylaldehyde was added. A precipitate formed. The reaction mixture was then heated to 80° C. to dissolve the precipitate. To this mixture, 132 grams of 1,5-dibromopentane was added over a period of one hour. The mixture was maintained at 80° C. for 8 hours, followed by cooling to 25° C. and the addition of 118 grams of hydroxylamine hydrochloride and 112 grams of potassium hydroxide. The reaction temperature rose to 50° C. After cooling to 40° C., this temperature was maintained for two hours. The mixture was then cooled to 25° C. and 1,565 grams of water was added. The mixture was stirred for 15 minutes, filtered, and the precipitate was dried to give 189 grams of 2-(5-[2-(hydroxyiminomethyl)phenoxy] pentyloxy)benzaldehyde oxime.

Step II

Synthesis of 2-(5-[2-(hydroxyiminomethyl)phenoxy] pentyloxy)benzaldehyde oxime dimethacrylate ester In a flask equipped with a stirrer, nitrogen inlet, cooling bath, and addition funnel, 189 grams of 2-(5-[2-(hydroxyiminomethyl)phenoxy]pentyloxy)benzaldehyde oxime (prepared in Step I of Example 1), 1,817 grams of tetrahydrofuran, and 124 grams of triethylamine was placed. The solution was cooled to 0° C. and 127 grams of methacryloyl chloride was added over a period of 45 minutes while maintaining the temperature below 15° C. The mixture was held at 15° C. for 30 minutes following completion of the addition of the methacryloyl chloride. Then, the mixture was allowed to warm to room temperature.

To the room temperature mixture, 363 grams of hexane and 727 grams of water were added. The resulting mixture was stirred for 15 minutes. After stirring, the phases were allowed to separate into an aqueous phase and an organic phase. The aqueous phase was discarded. The organic phase was washed with a premix of 191 grams of concentrated hydrochloric acid and 727 grams of water followed by 2 water washes of 363 grams each.

Phenothiazine was added to the organic phase. The solvent was removed using a rotary evaporator. To the resulting solid, a premix of 128 grams of ethyl acetate and 283 grams of hexane was added. The slurry was stirred, filtered, and washed with hexane. The resulting solid was dried, yielding 170 grams of 2-(5-[2-(hydroxyiminomethyl)phenoxy] pentyloxy)benzaldehyde oxime dimethacrylate ester.

Example 2

Step I
Synthesis of 2-(5-[2-(hydroxyiminomethyl)phenoxy]hexyloxy)benzaldehyde oxime The same procedure described in Example 1, Step I was followed, except using 334 grams of salicylaldehyde and 225 grams of dibromohexane in place of the dibromopentane and hydroxylamine hydrochloride. The reaction yielded 285 grams of 2-(5-[2-(hydroxyiminomethyl)phenoxy]hexyloxy)benzaldehyde oxime.

Step II
Synthesis of 2-(5-[2-(hydroxyiminomethyl)phenoxy]hexyloxy)benzaldehyde oxime diacrylate ester The same procedure described in Example 1, Step II was followed, except using 285 grams of 2-(5-[2-hydroxyiminomethyl)phenoxy]hexyloxy)benzaldehyde oxime (prepared in Step I of this example) and 172 grams acryloyl chloride. The reaction yielded 227 grams of 2-(5-[2-(hydroxyiminomethyl)phenoxy]hexyloxy)benzaldehyde oxime diacrylate ester instead of 2-(5-[2-(hydroxyiminomethyl)phenoxy]pentyloxyl benzaldehyde oxime and methacryloyl chloride, respectively.

Example 3

Step I
Synthesis of 2-(5-[2-(hydroxyiminomethyl)phenoxy]pentyloxy)benzaldehyde oxime The same procedure described in Example 1, Step I was followed.

Step I
Synthesis of 2-(5-[2-(hydroxyiminomethyl)phenoxy]pentyloxy)benzaldehyde oxime diacrylate ester The same procedure described in Example 1, Step II was followed, except that acryloyl chloride was used in place of methacryloyl chloride.

Example 4

Step I
Synthesis of 2-(5-[2-(hydroxyiminomethyl)phenoxy]propyloxy)benzaldehyde oxime The same procedure described in Example 1, Step I was followed, except that 1,3-dibromopropane was used in place of 1,5-dibromopentane.

Step II
Synthesis of 2-(5-[2-(hydroxyiminomethyl)phenoxy]propyloxy)benzaldehyde oxime dimethacrylate ester The same procedure described in Example 1, Step II was followed.

Example 5

Step I
Synthesis of 2-(5-[2-(hydroxyiminomethyl)phenoxy]propyloxy)benzaldehyde oxime The same procedure described in Example 4, Step I was followed.

Step II
Synthesis of 2-(5-[2-(hydroxyiminomethyl)phenoxy]propyloxy)benzaldehyde oxime diacrylate ester The same procedure described in Example 2, Step II was followed.

Example 6

Step I
Synthesis of 2-(5-[2-(hydroxyiminomethyl)phenoxy]butyloxy)benzaldehyde oxime The same procedure described in Example 1, Step I was followed except that 1,4-dibromobutane was used in place of 1,5-dibromopentane.

Step II
Synthesis of 2-(5-[2-(hydroxyiminomethyl)phenoxy]propyloxy)benzaldehyde oxime dimethacrylate ester The same procedure described in Example 1, Step II was followed.

Example 7

Step I
Synthesis of 2-(5-[2-(hydroxyiminomethyl)phenoxy]butyloxy)benzaldehyde oxime The same procedure described in Example 6, Step I was followed.

Step II
Synthesis of 2-(5-[2-(hydroxyiminomethyl)phenoxy]butyloxy)benzaldehyde oxime diacrylate ester The same procedure described in Example 2, Step II was followed.

Example 8

Step I
Synthesis of 2-(5-[2-(hydroxyiminomethyl)naphthoxy]decyloxy)naphthylaldehyde oxime The same procedure described in Example 1, Step I was followed except that 2-hydroxy-1-naphthaldehyde was used in place of salicylaldehyde and 1,10-dibromodecane was used in place of 1,5-dibromopentane.

Step II
Synthesis of 2-(5-[2-(hydroxyiminomethyl)naphthoxy]decyloxy)naphthylaldehyde oxime dimethacrylate ester The same procedure described in Example 1, Step II was followed.

Example 9

Step I
Synthesis of 3,5-dimethyl-2-(5-[2-(hydroxyiminomethyl)3,5-dimethylphenoxy]pentyloxy)benzaldehyde oxime The same procedure described in Example 1, Step I was followed except that 2,4-dimethyl-6-hydroxybenzaldehyde was used in place of salicylaldehyde.

Step II
Synthesis of 3,5-dimethyl-2-(5-[2-(hydroxyiminomethyl)3,5-dimethylphenoxy]pentyloxy)benzaldehyde oxime dimethacrylate ester The same procedure described in Example 1, Step II was followed.

Example 10

Step I
Synthesis of 4-hydroxy-4-methyl-2-pentanone oxime

In a flask equipped with a stirrer, nitrogen inlet, reflux condenser, and addition funnel, 100 milliliters of methanol, 20.0 grams of diacetone alcohol (4-hydroxy-4-methyl-2-pentanone), and 23.7 grams of finely ground sodium carbonate were placed. To this stirred mixture, 14.4 grams of hydroxylamine hydrochloride was added. The reaction temperature rose slightly and the mixture was stirred for 2.5 hours.

The mixture was then filtered, the precipitate was discarded, and the solvent was removed from the filtrate. The resulting solid was dissolved in 150 milliliters of tetrahydrofuran and filtered to remove additional precipitate. The tetrahydrofuran was removed using a rotary evaporator to yield 4-hydroxy-4-methyl-2-pentanone oxime.

Step II
Synthesis of 4-hydroxy-4-methyl-2-pentanone oxime diacrylate

In a flask equipped with a stirrer, nitrogen inlet, cooling bath, and addition funnel, 5.0 grams of 4-hydroxy-4-methyl-2-pentanone oxime (prepared in Step I of this example), 40 milliliters of tetrahydrofuran, and 8.0 grams of triethylamine were placed. The solution was cooled to 5° C. Then, a solution of 7.05 grams of acryloyl chloride dissolved in 20 milliliters of tetrahydrofuran was added over a period of 1.5 hours. The mixture was allowed to warm to room temperature and stirred for two hours. The tetrahydrofuran was removed.

The resulting solid was extracted twice with 50 milliliters of ethyl acetate, washed with a saturated aqueous solution of sodium chloride, dried over magnesium sulfate, and filtered. The solvent was removed to yield 4.7 grams of 4-hydroxy-4-methyl-2-pentanone oxime diacrylate.

Example 11

Step I
Synthesis of 2-(5-[2-(hydroxyiminomethyl)phenoxy] pentyloxy)benzaldehyde oxime The same procedure described in Example 1, Step I was followed.

Step II
Synthesis of 4,5-dichlorophthalic anhydride

In a flask equipped with a stirrer, nitrogen inlet, and DEAN-STARK trap, 10.0 grams of 4,5-dichlorophthalic acid, 150 milliliters of xylene, and several crystals of toluenesulfonic acid were added. The mixture was heated to reflux and water was collected in the DEAN-STARK trap over a period often hours. The xylene was distilled off and the solid was collected in a BÜCHNER funnel and allowed to air dry, yielding 8.3 grams of 4,5-dichlorophthalic anhydride.

Step III
Synthesis of 1-acryloxy-2-propyl-4,5-dichlorophthalate

In a flask equipped with a stirrer, nitrogen inlet, reflux condenser, and addition funnel, 4.5 grams of 2-hydroxypropylacrylate, 3.4 grams of triethyl amine, and 25 milliliters of tetrahydrofuran were added. To this stirred mixture, a solution of 6.9 grams of 4,5-dichlorophthalic anhydride (prepared in Step II of this Example) dissolved in 55 milliliters of tetrahydrofuran was added over a period of 0.5 hour. The resulting mixture was stirred for 18 hours.

Trace amounts of the inhibitors, MEHQ and phenothiazine, were added and the tetrahydrofuran solvent was removed using a rotary evaporator. The resulting solid was dissolved in 150 milliliters of ethyl acetate and 50 milliliters of dilute (3%) aqueous hydrochloric acid solution. The mixture was washed with water and a saturated aqueous sodium chloride solution. The mixture was separated into an aqueous phase and an organic phase. The organic phase was dried over $MgSO_4$ and filtered. The solvent was removed using a rotary evaporator at 30° C. to yield 10.5 grams of 1-acryloxy-2-propyl-4,5-dichlorophthalate.

Step IV
Synthesis of bis-(1,5-pentanedioxy-2-benzaldehydeoxime)-1-acryloxy-2-propyl-4,5-dichlorophthalyl 4,5-dichlorophthalate In a flask equipped with a stirrer and a nitrogen inlet, 1.0 gram of 2-(5-[2-(hydroxyiminomethyl)phenoxy]pentyloxy) benzaldehyde oxime (prepared in Step I), 3.46 grams of 1-acryloxy-2-propyl-4,5-dichlorophthalate (prepared in Step III), and 50 milliliters of ethyl acetate were placed. The resulting mixture was stirred to form a solution. A solution of 3.35 grams of dicyclohexylcarbodiimide in 15 milliliters of ethyl acetate was added to the stirred oxime solution. The resulting mixture was stirred for 18 hours, filtered, and the solvent was removed using a rotary evaporator at 30° C. to yield bis-(1,5-pentanedioxy-2-benzaldehydeoxime)-1-acryloxy-2-propyl-4,5-dichlorophthalyl 4,5-dichlorophthalate.

Example 12

Step I
Synthesis of 2-(5-[2-(hydroxyiminomethyl)phenoxy] pentyloxy)benzaldehyde oxime The same procedure described in Example 1, Step I was followed.

Step II
Synthesis of 1-acryloxy-2-propyl phthalate

The same procedure described in Example 11, Step III was followed except phthalic anhydride was used instead of 4,5-dichloro phthalic anhydride.

Step III
Synthesis of bis-(1,5-pentanedioxy-2-benzaldehydeoxime)-1-acryloxy-2-propylphthalyl phthalate The same procedure described in Example 11, Step IV was followed except 1-acryloxy-2-propyl phthalate was used instead of 1-acryloxy-2-propyl-4,5-dichloro phthalate.

Example 13

Synthesis of Salicylaldoxime Dimethacrylate Ester

In a flask equipped with a stirrer, a nitrogen inlet, and an addition funnel, 13.7 grams of salicylaldoxime and 150 milliliters of tetrahydrofuran were placed. The resulting stirred solution was cooled with an ice water bath to 5° C. Then, 30.8 grams of triethylamine was slowly added. To this solution, 30.0 grams of methacryloyl chloride was added over a period of one hour while maintaining the temperature at 5° C. After 10 minutes of mixing, 100 milliliters of hexane was added, followed by 100 milliliters of water (the temperature was kept below 10° C. during the water addition).

The resulting mixture was allowed to separate into an aqueous phase and an organic phase. The aqueous phase was separated and discarded. The organic phase was dried over sodium sulfate. A trace of phenothiazine was added and the solvent was removed using a rotary evaporator. The resulting residue was purified by column chromatography on a silica gel column eluted with a 1:1 mixture of hexane and ethyl acetate to yield 7.8 grams of salicylaldoxime dimethacrylate ester.

Example 14

Synthesis of 3-(2-hydroxyethoxy)benzaldoxime dimethacrylate ester

In a flask equipped with a stirrer, a nitrogen inlet, and an addition funnel, 5.17 grams of 3-(2-hydroxyethoxy) benzaldoxime, 6.36 grams of triethylamine, and 150 milliliters of tetrahydrofuran were placed. The resulting solution was cooled to 0° C. Then, 8.95 grams of methacryloyl chloride was slowly added. The mixture was warmed to room temperature and stirred for one hour. To this mixture, 150 milliliters of hexane and 75 milliliters of water were added. The aqueous phase was removed and the organic phase was washed with a 3% aqueous hydrochloric acid (HCl) solution followed by washing with a saturated aqueous sodium chloride solution. The organic layer was dried over anhydrous magnesium sulfate and the solvent was removed to yield 2.6 grams of 3-(2-hydroxyethoxy) benzaldoxime dimethacrylate ester.

Example 15

Synthesis of Terephthalaldoxime Dimethacrylate Ester

In a flask equipped with a stirrer, a nitrogen inlet, and an addition funnel, 3.3 grams of terephthalaldoxime, 4.9 grams of triethyl amine, and 40 milliliters of tetrahydrofuran were placed. The resulting solution was cooled with an ice water bath to 5° C. Then, 5.0 grams of methyacryloylchloride was added over a period of 15 minutes. The mixture was stirred for one hour followed by the slow addition of 30 milliliters of water. The solid formed was filtered and washed with a 1:1 water and acetone mixture to give, after drying, 2.3 grams of terephthaldoxime dimethacrylate ester.

Example 16
Synthesis of 2-(5-[2-(hydroxyiminomethyl)phenoxy]hexyloxy)benzaldehyde oxime di-2-acryloxyethylcarbonate In a flask cooled by an ice water bath and equipped with a stirrer, a nitrogen inlet, a dry ice condenser, and a caustic scrubber, 12 grams of phosgene was placed. To this mixture, a solution of 8.4 grams of 2-methyl-2-butene in 50 milliliters of tetrahydrofuran (precooled in an ice water bath) was slowly added. To the resulting 5° C. mixture, 12.8 grams of 2-hydroxyethyl acrylate was added over a period of 30 minutes. During the addition, the mixture temperature was maintained below 8° C. The mixture was warmed to 22° C. and 20 milliliters of solvent was removed using a stream of nitrogen vented through the scrubber. A vacuum, via a water aspirator, was then applied and the remainder of the solvent was removed to yield the chloroformate ester of 2-hydroxyethyl acrylate.

The chloroformate ester of 2-hydroxyethyl acrylate was added to a 5° C. solution of 13 grams of 2-(5-[2-(hydroxyiminomethyl)phenoxy]hexyloxy)benzaldehyde oxime (prepared in Example 2, Step I) in 50 milliliters of tetrahydrofuran over 40 minutes (the temperature was maintained at 10–15° C. throughout the addition). The reaction was slowly warmed to 22° C., stirred for 30 minutes, and 30 milliliters of 3% aqueous HCl and 30 milliliters of ethyl acetate were added. To the resulting emulsion, 50 milliliters of ethyl acetate and 30 milliliters of hexane were added.

The resulting mixture was allowed to separate into an aqueous phase and an organic phase. The aqueous phase was separated and discarded. The organic phase was separated, washed with aqueous potassium chloride, and dried over sodium sulfate. The solvent was removed and the solid residue was washed with 50 milliliters of a 1:1 mixture of hexane and ethyl acetate to give 10.5 grams of a white solid that was recrystallized from ethyl acetate and hexane to yield 8.4 grams of 2-(5-[2-(hydroxyiminomethyl)phenoxy]hexyloxy)benzaldehyde oxime di-2-acryloxyethylcarbonate.

Example 17
Synthesis of 6-(3-[(ethylamino)carbonyl]-3-butenoyloxy)hexyl 3-[(ethylamino)carbonyl]-3-butenoate In a flask equipped with a stirrer, nitrogen inlet, and addition funnel, 11.2 grams of itaconic anhydride, 5.9 grams of 1,6-dihydroxyhexane, and 0.1 gram of phenothiazine were placed. The resulting mixture was heated on a steam bath for 3 hours. The mixture was cooled and 50 milliliters of chloroform and 13 grams of thionyl chloride were added. The mixture was heated at reflux for one hour. The solvent was then removed under vacuum. Heptane was added and then stripped to remove the last traces of thionyl chloride. The residue was slowly added to a solution of 11.8 grams of n-propylamine in 75 milliliters of tetrahydrofuran. The reaction was cooled throughout the addition so as to maintain a temperature of 20° C. After the addition was complete, the mixture was stirred for 15 minutes. Then, 50 milliliters of 1% aqueous hydrochloric acid and 50 milliliters of ethyl acetate were added.

The organic phase was separated, washed with saturated potassium chloride solution, and dried over sodium sulfate. The solvent was removed under vacuum and the residue recrystallized from ethyl acetate/hexane to yield 4.3 grams of 6-(3-[(ethylamino)carbonyl]-3-butenoyloxy)hexyl 3-[(ethylamino)carbonyl]-3-butenoate.

Examples 18–32

Polymers containing degradable crosslinkers were prepared and tested according to the Gel Test method. The type and amount of the degradable crosslinker used is noted in Table 1. The results of the Gel Test are provided in Tables 2–4. Time and temperature for each Gel Test are noted in the Tables.

TABLE 1

| Example | Example Number Describing Crosslinker Used | Crosslinker Amount (parts by weight) |
|---|---|---|
| 18A | 1 | 0.25 |
| 18B | 1 | 0.50 |
| 19A | 2 | 0.25 |
| 19B | 2 | 0.50 |
| 20A | 3 | 0.25 |
| 20B | 3 | 0.50 |
| 21 | 4 | 0.50 |
| 22 | 5 | 0.50 |
| 23 | 6 | 0.50 |
| 24 | 7 | 0.50 |
| 25A | 8 | 0.25 |
| 25B | 8 | 0.50 |
| 26 | 9 | 0.50 |
| 27A | 14 | 0.25 |
| 27B | 14 | 0.50 |
| 28A | 15 | 0.25 |
| 28B | 15 | 0.50 |
| 29A | 17 | 0.10 |
| 29B | 17 | 0.25 |
| 29C | 17 | 0.50 |
| 29D | 17 | 1.00 |
| 30A | 11 | 0.50 |
| 30B | 11 | 1.00 |
| 31A | 12 | 0.50 |
| 31B | 12 | 1.00 |
| 32A | 16 | 0.50 |
| 32B | 16 | 0.75 |

TABLE 2

| Example | % Gel initial | % Gel after 1 minute at 175° C. | % Gel after 5 minutes at 175° C. |
|---|---|---|---|
| 18A | 78 | 21 | 1 |
| 18B | 74 | 29 | 3 |
| 19A | 61 | 43 | 0 |
| 19B | 80 | 64 | 1 |
| 20A | 75 | 55 | 6 |
| 20B | 73 | 68 | 11 |
| 21 | 78 | 33 | 2 |
| 22 | 90 | 56 | 3 |
| 23 | 75 | 2 | 2 |
| 24 | 95 | 68 | 1 |
| 25A | 52 | 47 | 41 |
| 25B | 70 | 68 | 68 |
| 26 | 57 | 11 | 3 |
| 27A | 82 | 82 | 39 |
| 27B | 86 | 89 | 40 |
| 28A | 55 | 7 | 3 |
| 28B | 62 | 5 | 3 |

TABLE 3

| Example | % Gel initial | % Gel after 30 seconds at 175° C. | % Gel after 45 seconds at 175° C. | % Gel after 1 minute at 175° C. | % Gel after 2 minutes at 175° C. |
|---|---|---|---|---|---|
| 30A | 68 | 15 | 0 | 0 | ND |
| 30B | 74 | 21 | 0 | 0 | ND |
| 31A | 70 | 65 | ND | 17 | 1 |
| 31B | 82 | 78 | ND | 40 | 1 |
| 32A | 71 | 71 | 44 | ND | 3 |

TABLE 3-continued

| Example | % Gel initial | % Gel after 30 seconds at 175° C. | % Gel after 45 seconds at 175° C. | % Gel after 1 minute at 175° C. | % Gel after 2 minutes at 175° C. |
|---|---|---|---|---|---|
| 32B | 82 | 78 | 62 | ND | 2 |

ND = Not Determined

TABLE 4

| Example | % Gel initial | % Gel after 1 minute at 180° C. | % Gel after 5 minutes at 180° C. |
|---|---|---|---|
| 29A | 83 | 77 | 66 |
| 29B | 91 | 86 | 79 |
| 29C | 96 | 96 | 91 |
| 29D | 97 | 98 | 94 |

Comparative Examples C1–C7

Polymers were prepared according to the Gel Test method, except the polymers either contained a non-degradable crosslinker or no crosslinker, as noted in Table C1. Results of the Gel Test are also provided in Table C1.

TABLE C1

| Example | Crosslinker | Crosslinker Amount (parts by weight) | % Gel initial | % Gel after 1 minute at 175° C. | % Gel after 5 minutes at 175° C. |
|---|---|---|---|---|---|
| C1 | None | 0 | 6 | 7 | 11 |
| C2 | HDDA | 0.10 | 89 | 92 | 83 |
| C3 | HDDA | 0.25 | 89 | 96 | 88 |
| C4 | HDDA | 0.50 | >95 | >95 | 94 |
| C5 | HDDMA | 0.10 | 72 | 78 | 70 |
| C6 | HDDMA | 0.25 | 60 | 88 | 87 |
| C7 | HDDMA | 0.50 | 88 | >95 | 90 |

Examples 33–43

A suspension-polymerized crosslinked polymer composition was prepared according to the method described in European Patent Application No. EP 0 853 092 (Minnesota Mining & Manufacturing Co.) with the following modifications:

The reaction was carried out in a flask equipped with a condenser, thermowell, nitrogen inlet, stainless steel motor-driven agitator, and a heating mantle with temperature control. To the reaction flask, 450 parts of deionized water and 36 parts of methylcellulose stabilizer (17,000 grams/mole) were added. The reaction flask was heated to, and maintained at, 45° C. while the contents were agitated and purged with nitrogen.

A premix containing the (meth)acrylate monomers, degradable crosslinker, and other ingredients shown in Table 5 (amounts are in parts by weight) was added to the reaction flask while stirring vigorously at a rate of about 500 to about 950 revolutions per minute. The temperature of the reaction mixture was adjusted to 55° C., the nitrogen purge was maintained, and the reaction was allowed to continue to completion. The resulting, roughly 85% solids, partially tacky crosslinked polymer beads were collected by filtration. The partially dried beads were mixed with 1 part of AEROSIL R-972. The resulting beads were then further dried, either by air evaporation or vacuum drying at 70° C., to give free-flowing beads.

TABLE 5

| Ex. | (Meth)acrylate Monomers (parts) | Example Number Describing Crosslinker Used | Cross-linker Amount (parts) | VAZO 52 (parts) | ABP (parts) | IOTG (parts) |
|---|---|---|---|---|---|---|
| 33 | AA/MAA/EHA (30/15/255) | 1 | 3.0 | 0.90 | 3 | 0.38 |
| 34 | AA/MAA/EHA (22.5/15/262.5) | 1 | 3.0 | 0.90 | 3 | 0.3 |
| 35 | AA/MAA/IOA (19.5/16.5/264) | 1 | 1.5 | 1.00 | 3 | 0.18 |
| 36 | AA/MAA/IOA (22.5/15/262.5) | 1 | 1.5 | 1.00 | 4.2 | 0.30 |
| 37 | AA/MAA/EHA/nOA (15/15/240/30) | 1 | 1.5 | 0.90 | 3 | 0.30 |
| 38 | AA/MAA/EHA (22.5/15/262.5) | 1 | 1.5 | 0.90 | 3 | 0.30 |
| 39 | AA/MAA/EHA (22.5/15/262.5) | 1 | 3.0 | 0.90 | — | 0.23 |
| 40 | MAA/EHA (36/264) | 1 | 3.0 | 0.90 | 3 | 0.30 |
| 41 | nBA/IBA (105/165) | 1 | 3.0 | 0.9 | 3 | 0.075 |
| 42 | AA/MAA/IOA (21/18/261) | 1 | 1.5 | 1.00 | 1.8 | 0.30 |
| 43 | AA/MAA/EHA (22.5/15/262.5) | 2 | 1.5 | 0.9 | 3 | 0.3 |

Example 44

The reaction was carried out in a flask equipped with a condenser, thermowell, nitrogen inlet, stainless steel motor-driven agitator, and a heating mantle with temperature control. To the reaction flask, 150 parts of deionized water, including 0.6 part of methyl cellulose stabilizer (17,000 grams/mole), was added. The reaction flask was heated to, and maintained at, 45° C. while the contents were agitated and purged with nitrogen.

A premix containing 87.5 parts EHA, 5 parts MAA, 7.5 parts AA, 1 part of the degradable crosslinker prepared in Example 1, 0.25 part ABP, and 0.075 part IOTG was added to the reaction flask while the mixture was stirred vigorously at a rate of about 500 to about 950 revolutions per minute. The temperature of the reaction mixture was adjusted to 80° C., the nitrogen purge was maintained, and the reaction was allowed to continue to completion. The resulting, roughly 85% solids, partially tacky crosslinked polymer beads were collected by filtration. The partially dried beads were mixed with 1 part of AEROSIL R-972. The resulting beads were further dried by air evaporation to give free-flowing beads having a gel content of 66%.

Example 45

A sample (designated HMM+Press) of the free-flowing beads prepared in Example 44 was placed in a hot-melt mixer and heated to 175° C. to activate the degradable crosslinker. The hot-melt mixer contained three chambers and a valve to discharge mixed polymer. The three chambers were configured as upper, middle, and lower chambers. The middle chamber contained the valve for discharge of the mixed polymer and the static mixing elements. All three chambers were heated.

Free-flowing beads were placed in the top chamber. A heating period then transferred heat from the chamber walls to the beads. A piston drove beads from the upper chamber, through the middle chamber over the static mixing elements, and into the bottom chamber. After the beads had fully entered the bottom chamber, a piston in the bottom chamber forced the beads back through the middle chamber and across the static mixing elements again. This process was repeated as many times as was necessary to adequately mix the beads.

The mixed, heated beads were pressed between two siliconized liners in a hot-melt press set at 175° C. and pressed at 69 MegaPascals for 2 minutes. One of the liners was removed and the exposed sample was then laminated to a 37-micrometer-thick, aminated, polybutadiene-primed polyester film.

A separate sample (designated "Press") of the free-flowing beads prepared in Example 44 was coated between liners in the same manner, but was not hot-melt-mixed before coating. The sample was also placed in a hot-melt press set at 175° C. After sitting for 5 minutes, the sample was pressed at 69 MegaPascals for 2 minutes.

For the "HMM+Press" and "Press" methods, the samples were removed from the press and the siliconized polyester liner was removed. The resulting samples each had an adhesive thickness of 64–89 micrometers.

Additional samples (Examples 45B–D and 45F–H) were further cured using a Fusion Systems (Gaithersburg, Md.) ultraviolet (UV) processor with an "H" bulb lights at the UV dosages listed in Table 6. The samples were then tested for 180° Peel Adhesion and Shear Strength following the test methods described above.

TABLE 6

| Ex. | Processing Method | UV Dosage (mJ/cm$^2$) | % Gel | 180° Peel Adhesion (N/dm) | Shear Strength (minutes) | Failure Mode |
|---|---|---|---|---|---|---|
| 45A | Press | 0 | ND | 53.4 | 32 | C |
| 45B | Press | 140 | 64 | 44.6 | 60 | A |
| 45C | Press | 280 | 73 | 58.2 | 80 | A |
| 45D | Press | 420 | ND | 51.2 | 82 | A |
| 45E | HMM + Press | 0 | ND | 74.4 | 24 | C |
| 45F | HMM + Press | 140 | 75 | 65.2 | 97 | A |
| 45G | HMM + Press | 280 | 84 | 51.6 | 204 | A |
| 45H | HMM + Press | 420 | ND | 56.5 | 99 | A |

ND = Not Determined

Example 46

A sample of the free-flowing beads prepared in Example 44 was placed in the hot-melt mixer described in Example 45 and mixed and heated to 175° C. to activate the degradable crosslinkers. The mixture was allowed to cool to room temperature and was then dissolved in ethyl acetate to give a 35% solids solutions.

To a sample of the solution, 1 part PIC was added. The solution was solvent-coated onto a 37-micrometer-thick, aminated, polybutadiene-primed, polyester film and dried in a 70° C. oven for 20 minutes. The resulting adhesive coating had a thickness of 50 micrometers. Additional samples (Examples 46B–D and 46F–H) were further cured using a Fusion Systems ultraviolet (UV) processor with an "HT" bulb at the UV dosages listed in Table 7. Samples of the resulting tapes were tested for 180° Peel Adhesion, Gel, and Shear Strength according to the test methods described above.

TABLE 7

| Ex. | PIC (parts) | UV Dosage (mJ/cm$^2$) | % Gel | 180° Peel Adhesion (N/dm) | Shear Strength (minutes) | Failure Mode |
|---|---|---|---|---|---|---|
| 46A | 0 | 0 | ND | 69.6 | 26 | C |
| 46B | 0 | 140 | 83 | 50.5 | 592 | A |
| 46C | 0 | 280 | 86 | 55.1 | 316 | A |
| 46D | 0 | 420 | ND | 56.5 | 672 | A |
| 46E | 1 | 0 | ND | 54.5 | 30 | C |
| 46F | 1 | 140 | 86 | 64.8 | 1,013 | A |
| 46G | 1 | 280 | 88 | 43.8 | 1,702 | A |
| 46H | 1 | 420 | ND | 50.5 | 959 | A |

ND = Not Determined

Example 47

A sample of the free-flowing beads prepared in Example 44 was placed in the hot-melt mixer described in Example 45 and mixed and heated to 175° C. to activate the degradable crosslinker and form a molten polymer. The molten polymer was then coated onto a 37-micrometer-thick, aminated, polybutadiene-primed, polyester film. The resulting adhesive coating had a thickness of 25–50 micrometers To another sample of the molten polymer, 1 part PIC was added before placing it in the extruder and coating it as described above. Additional samples (Examples 47B–D and 47F–H) were further cured using a Fusion Systems ultraviolet (UV) processor with an "H" bulb at the UV dosages listed in Table 8 Samples of the resulting tapes were tested for 180° Peel Adhesion, Gel, and Shear Strength according to the test methods described above.

TABLE 8

| Ex. | PIC (parts) | UV Dosage (mJ/cm$^2$) | % Gel | 180° Peel Adhesion (N/dm) | Shear Strength (minutes) | Failure Mode |
|---|---|---|---|---|---|---|
| 47A | 0 | 0 | ND | 56.0 | 64 | C |
| 47B | 0 | 140 | 83 | 54.7 | 1,664 | A |
| 47C | 0 | 280 | 87 | 48.8 | 2,135 | A |
| 47D | 0 | 420 | ND | 53.6 | 2,229 | A |
| 47E | 1 | 0 | ND | 61.5 | 41 | C |
| 47F | 1 | 140 | ND | 53.6 | 1,200 | A |
| 47G | 1 | 280 | ND | 48.4 | 757 | A |
| 47H | 1 | 420 | ND | 44.9 | 886 | A |

ND = Not Determined

Example 48

A sample of the free-flowing beads prepared in Example 44 was placed in an extruder and coated onto a 37-micrometer-thick, aminated, polybutadiene-primed, polyester film. The resulting adhesive coating had a thickness of 38 micrometers. Another sample of the free-flowing beads prepared in Example 44 was co-extruded with 1 part PIC and also coated as described above. Additional samples (Examples 48B–D and 48F–H) were further cured using a Fusion Systems ultraviolet (UV) processor with an "H" bulb at the UV dosages listed in Table 9. Samples of the resulting tapes were tested for Shear Strength according to the test method described above.

TABLE 9

| Example | PIC (parts) | UV Dosage (mJ/cm$^2$) | Shear Strength (minutes) | Failure mode |
|---------|-------------|-----------------------|--------------------------|--------------|
| 48A | 0 | 0 | 37 | C |
| 48B | 0 | 140 | 345 | A |
| 48C | 0 | 280 | 336 | A |
| 48D | 0 | 420 | 435 | A |
| 48E | 1 | 0 | 31 | C |
| 48F | 1 | 140 | 656 | A |
| 48G | 1 | 280 | 415 | A |
| 48H | 1 | 420 | 469 | A |

Various modifications and alterations of the invention will become apparent to those skilled in the art without departing from the spirit and scope of the invention, which is defined by the accompanying claims. It should be noted that steps recited in any method claims below do not necessarily need to performed in the order that they are recited. Those of ordinary skill in the art will recognize variations in performing the steps from the order in which they are recited.

What is claimed is:

1. A degradable crosslinker comprising:
   at least one energetically labile moiety; and
   at least two free radically polymerizable groups,
   wherein after incorporation into a polymer the degradable crosslinker fragments into at least two fragments upon activation by an external energy source, wherein the at least two fragments are essentially free of free radicals and ethylenic unsaturation.

2. The degradable crosslinker of claim 1, wherein the crosslinker comprises at least two energetically labile moieties.

3. The degradable crosslinker of claim 1, wherein the crosslinker comprises at least two different energetically labile moieties.

4. The degradable crosslinker of claim 1, wherein the crosslinker is storage-stable.

5. The degradable crosslinker of claim 1, wherein the crosslinker is a thermally degradable crosslinker.

6. The degradable crosslinker of claim 1, wherein the crosslinker is a (meth)acrylate degradable crosslinker.

7. The degradable crosslinker of claim 1, wherein the crosslinker comprises an ester moiety.

8. The degradable crosslinker of claim 1, wherein the crosslinker comprises an amide ester moiety.

9. The degradable crosslinker of claim 1, wherein the crosslinker comprises at least one of an aldoxime ester or an aldoxime carbonate moiety.

10. A crosslinked polymer composition comprising:
    at least one polymer; and
    at least one degradable crosslinker of claim 1 incorporated into the at least one polymer.

11. The crosslinked polymer composition of claim 10, wherein at least two degradable crosslinkers are incorporated into the at least one polymer.

12. The crosslinked polymer composition of claim 10, further comprising at least one non-degradable crosslinker.

13. The crosslinked polymer composition of claim 10, wherein the composition is essentially nontacky at room temperature.

14. The crosslinked polymer composition of claim 10, wherein the composition is at least partially tacky at room temperature.

15. The crosslinked polymer composition of claim 10, wherein the composition is free-flowing.

16. The crosslinked polymer composition of claim 10, further comprising at least one of a dusting agent and a coating agent.

17. A substrate at least partially coated with the crosslinked polymer composition of claim 10.

18. A method of transitioning a crosslinked polymer composition from a first chemical state to a second chemical state, the method comprising the steps of:
    providing the crosslinked polymer composition of claim 10, and
    activating at least a portion of the crosslinked polymer composition to fragment at least a portion of the degradable crosslinker by applying an external energy source to at least a portion of the crosslinked polymer composition.

19. The method of claim 18, wherein the external energy source is a thermal energy source.

20. The method of claim 18, further comprising the step of catalyzing fragmentation of the degradable crosslinker.

21. The method of claim 18, further comprising the step of applying the crosslinked polymer composition to at least a portion of a substrate.

22. The method of claim 21, wherein the step of activating occurs prior to applying the crosslinked polymer composition to at least a portion of the substrate.

23. The method of claim 21, wherein the step of activating occurs while applying the crosslinked polymer composition to at least a portion of the substrate.

24. The method of claim 21, wherein the step of activating occurs after applying the crosslinked polymer composition to at least a portion of the substrate.

25. The method of claim 18, further comprising the step of recrosslinking at least a portion of the polymer composition.

26. A polymer composition comprising:
    a polymer; and
    at least two pendant moieties on the polymer, wherein the pendant moieties are the reaction product of fragmentation of the degradable crosslinker of claim 1 and wherein the pendant moieties comprise the at least two fragments that are essentially free of free radicals and ethylenic unsaturation.

27. A substrate at least partially coated with the polymer composition of claim 26.

* * * * *

UNITED STATES PATENT AND TRADEMARK OFFICE
CERTIFICATE OF CORRECTION

PATENT NO. : 6,652,970 B1  
DATED : November 25, 2003  
INVENTOR(S) : Everaerts, Albert I.

It is certified that error appears in the above-identified patent and that said Letters Patent is hereby corrected as shown below:

Title page,  
Item [56], References Cited, OTHER PUBLICATIONS,  
"Min Yu Li, et al," reference, please delete "2774" and insert in place thereof -- 2704 --.  
"*Kirk–Othmer Encyclopedia of Chemical Technology*," reference, please delete " "coating" and insert in place thereof -- "Coating --.

Column 1,  
Line 18, delete "hot-MELT" and insert in place thereof -- hot-melt --.  
Line 63, delete "is" before "that".

Column 2,  
Line 37, delete "(Hamer et" and insert in place thereof -- (Hamer et al.). --.

Column 7,  
Line 9, after "thereof" insert -- . --.

Column 11,  
Lines 10-15, delete the structure present and insert in place thereof

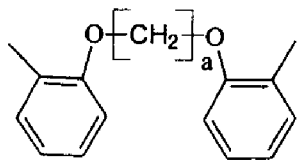

Column 15,  
Lines 28 and 58, after "thereof" insert -- . --.

Column 17,  
Line 37, after "thereof" insert -- . --.

Column 18,  
Line 62, delete "(martens et al.)," and insert in place thereof -- (Martens et al.), --.

Column 23,  
Line 35, delete "is" before "oven".

UNITED STATES PATENT AND TRADEMARK OFFICE
CERTIFICATE OF CORRECTION

PATENT NO. : 6,652,970 B1
DATED : November 25, 2003
INVENTOR(S) : Everaerts, Albert I.

It is certified that error appears in the above-identified patent and that said Letters Patent is hereby corrected as shown below:

Column 27,
Line 30, delete "Step I" and insert in place thereof -- Step II --.

Column 29,
Line 26, delete "often" and insert in place thereof -- of ten --.

Column 36,
Line 5, delete " "HT" " and insert in place thereof -- "H" --.
Line 33, after "micrometers" insert -- . --.

Signed and Sealed this

Thirteenth Day of September, 2005

JON W. DUDAS
*Director of the United States Patent and Trademark Office*